United States Patent
Fan et al.

(10) Patent No.: US 11,453,898 B1
(45) Date of Patent: Sep. 27, 2022

(54) **GENETICALLY ENGINEERED BACTERIUM OF *ESCHERICHIA COLI* AND METHOD FOR FERMENTATION PRODUCTION OF L-THEANINE THEREOF**

(71) Applicants: Henan Julong Biological Engineering Co., Ltd, Henan (CN); Tianjin University of Science and Technology, Tianjin (CN)

(72) Inventors: Xiaoguang Fan, Tianjin (CN); Xiaodong Liu, Henan (CN); Jing Li, Henan (CN); Ning Chen, Tianjin (CN); Bochao Liu, Henan (CN); Shuai Liu, Henan (CN); Chaochao Sun, Henan (CN); Yongchao Liu, Henan (CN); Jiajia Teng, Henan (CN); Mengtao Zhang, Henan (CN); Yuanqing Ji, Tianjin (CN); Yuhang Zhou, Tianjin (CN); Qingyang Xu, Tianjin (CN)

(73) Assignees: Henan Julong Biological Engineering Co., Ltd, Ruzhou (CN); Tianjin University of Science and Technology, Tianjin (CN)

( * ) Notice: Subject to any disclaimer, the term of this patent is extended or adjusted under 35 U.S.C. 154(b) by 0 days.

(21) Appl. No.: 17/566,702

(22) Filed: Dec. 31, 2021

(30) Foreign Application Priority Data

Sep. 30, 2021 (CN) .......................... 202111159099.6

(51) Int. Cl.
*C12P 13/14* (2006.01)
*C12N 15/70* (2006.01)
*C12N 1/00* (2006.01)

(52) U.S. Cl.
CPC .............. *C12P 13/14* (2013.01); *C12N 15/70* (2013.01); *C12N 1/00* (2013.01); *C12N 2510/00* (2013.01)

(58) Field of Classification Search
CPC ........... C12P 13/14; C12N 15/70; C12N 1/00; C12N 2510/00
See application file for complete search history.

(56) References Cited

FOREIGN PATENT DOCUMENTS

| CN | 102719367 B | 6/2013 |
|---|---|---|
| CN | 104087535 B | 1/2017 |
| CN | 105061249 B | 1/2017 |
| CN | 103409475 B | 3/2017 |
| CN | 109851520 A | 6/2019 |
| CN | 109370966 B | 4/2020 |
| CN | 109777763 B | 6/2020 |
| CN | 106893748 B | 11/2020 |

*Primary Examiner* — Iqbal H Chowdhury

(57) ABSTRACT

The present invention belongs to the bioengineering field, and relates to a method for fermentation production of L-theanine by using an *Escherichia coli* genetically engineered bacterium. The engineered bacterium is obtained by serving a strain as an original strain, wherein the strain is obtained after performing a single copy of T7RNAP, a dual copy of gmas, xylR knockout, and sucCD knockout on an *Escherichia coli* W3110 genome, and by integrating genes xfp, pta, acs, gltA, and ppc, and knocking out ackA on the genome. The present invention has a high yield, and stable production performance; after 20-25 h, L-theanine has a titer of 75-80 g/L, and the yield is up to 52-55%. The fermentation broth is purified by membrane separation in combination with a cation-anion resin series technique. Moreover, the one-step crystallization yield is 72.3% and the L-theanine final product has a purity of 99%.

3 Claims, 6 Drawing Sheets

Specification includes a Sequence Listing.

SEQUENCE LISTING

```
<160> NUMBER OF SEQ ID NOS: 53

<210> SEQ ID NO 1
<211> LENGTH: 2478
<212> TYPE: DNA
<213> ORGANISM: B. adolescentis ATCC 15703

<400> SEQUENCE: 1
atgacctctc cggttatcgg tacccgtgg aaaaaactga acgcgccggt ttctgaagaa      60
gcgatcgaag gtgttgacaa atactggcgt gcggcgaact acctgtctat cggtcagatc     120
tacctgcgtt ctaacccgct gatgaaagaa ccgttcaccc gtgaagacgt tagacaccgt     180
ctggttggtc actggggtac caccccgggt ctgaacttcc tgatcggtca catcaaccgt     240
ctgatcgcgg accaccagca gaacaccgtt atcatcatgg gtccgggtca cggtggtccg     300
gcgggtaccg cgcagtctta cctggacggt acctacaccg aatacttccc gaacatcacc     360
aaagacgaag cgggtctgca gaaattcttc cgtcagttct cttacccggg tggtatcccg     420
tctcactacg cgccggaaac cccgggttct atccacgaag gtgtgaact gggttacgcg     480 ctgtctcacg cgtacggtgc ggttatgaac aacccgtctc tgttcgttcc ggcgatcgtt     540
ggtgacggtg aagcggaaac cggtccgctg gcgaccggtt ggcagtctaa caaactgatc     600
aacccgcgta ccgacggtat cgttctgccg atcctgcacc tgaacggtta caaaatcgcg     660
aacccgacca tcctgtctcg tatctctgac gaagaactgc acgagttctt ccacggtatg     720
ggttacgaac cgtacgagtt cgttgcgggt ttcgacaacg aagaccacct gtctatccac     780
cgtcgtttcg cggaactgtt cgaaaccgtt ttcgacgaaa tctgcgacat caaagcggcg     840
```

```
gcgcagaccg acgacatgac ccgtccgttc tacccgatga tcatcttccg tacccgaaa      900
ggttggacct gcccgaaatt catcgacggt aaaaaaaccg aaggttcttg gcgttctcac     960
caggttccgc tggcgtctgc gcgtgacacc gaagcgcact tcgaagttct gaaaaactgg    1020
ctggaatctt acaaaccgga aaaactgttc gacgaaaacg gtgcggttaa accggaagtt    1080
accgcgttca tgccgaccgg tgaactgcgt atcggtgaaa cccgaacgc gaacggtggt     1140
cgtatccgtg aagaactgaa actgccgaaa ctggaagact acgaagttaa agaagttgcg    1200
gaatacggtc acggttgggg tcagctggaa gcgacccgtc gtctgggtgt ttacacccgt    1260
gacatcatca aaacaacccc ggactctttc cgtatcttcg gtccggacga aaccgcgtct    1320
aaccgtctgc aggcggcgta cgacgttacc aacaaacagt gggacgcggg ttacctgtct    1380
gcgcaggttg acgaacacat ggcggttacc ggtcaggtta ccgaacagct gtctgaacac    1440
cagatggaag gtttcctgga aggttacctg ctgaccggtc gtcacggtat ctggtcttct    1500
tacgaatctt tcgttcacgt tatcgactct atgctgaacc agcacgcgaa atggctggaa    1560
gcgaccgttc gtgaaatccc gtggcgtaaa ccgatctctt ctatgaacct gctggtttct    1620
tctcacgttt ggcgtcagga ccacaacggt ttctctcacc aggacccggg tgttacctct    1680
gttctgctga caaatgctt caacaacgac cacgttatcg gtatctactt cccggttgac    1740
tctaacatgc tgctggcggt tgcggaaaaa tgctacaaat ctaccaacaa aatcaacgcg    1800
atcatcgcgg gtaaacagcc ggcggcgacc tggctgaccc tggacgaagc gcgtgcggaa    1860
ctggaaaaag gtgcggcgga atggaaatgg gcgtctaacg ttaaatctaa cgacgaagcg    1920
cagatcgttc tggcggcgac cggtgacgtt ccgacccagg aaatcatggc ggcggcggac    1980
aaactggacg cgatgggtat caaattcaaa gttgttaacg ttgttgaacct ggttaaactg   2040
cagtctgcga agaaaaacaa cgaagcgctg tctgacgaag agttcgcgga actgttcacc    2100
gaagacaaac cggttctgtt cgcgtaccac tcttacgcgc gtgacgttcg tggtctgatc    2160
tacgaccgtc cgaaccacga caacttcaac gttcacggtt acgaagaaca gggttctacc    2220
accaccccgt acgacatggt tcgtgttaac aacatcgacc gttacgaact gcaggcggaa    2280
gcgctgcgta tgatcgacgc ggacaaatac gcggacaaaa tcaacgaact ggaagcgttc    2340
cgtcaggaag cgttccagtt cgcggttgac aacggttacg accacccgga ctacaccgac    2400
tgggtttact ctggtgttaa caccaacaaa cagggtgcga tctctgcgac cgcggcgacc    2460
gcgggtgaca acgaatga                                                  2478
```

<210> SEQ ID NO 2
<211> LENGTH: 2145
<212> TYPE: DNA
<213> ORGANISM: E. coli ATCC 27325

<400> SEQUENCE: 2

```
gtgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc    120
gctcagccgc gtaccggtgg cgatgcgccc gatcagacta cgactatcgt gcgtgcgaac    180
tcttccacca cgacggccgc tgaaccgctg aaaatgagct acgttgaagg tctgctttcc    240
agcaatcaga aagatgtgct gatggaagag atcgtcgcaa actaccacgc taacaccaaa    300
gacgctgaag tcgttctggt tgaaggtctg gtcccgacac gtaagcacca gtttgcccag    360
tctctgaact acgaaatcgc taaaacgctg aatgcgaaa tcgtcttcgt tatgtctcag    420
ggcactgaca ccccggaaca gctgaaagag cgtatcgaac tgacccgcaa cagcttcggc    480
```

```
ggtgccaaaa acaccaacat caccggcgtt atcgttaaca aactgaacgc accggttgat    540
gaacagggtc gtactcgccc ggatctgtcc gagattttcg acgactcttc caaagctaaa    600
gtaaacaatg ttgatccggc gaagctgcaa gaatccagcc cgctgccggt tctcggcgct    660
gtgccgtgga gctttgacct gatcgcgact cgtgcgatcg atatggctcg ccacctgaat    720
gcgaccatca tcaacgaagg cgacatcaat actcgccgcg ttaaatccgt cactttctgc    780
gcacgcagca ttccgcacat gctggagcac ttccgtgccg gttctctgct ggtgacttcc    840
gcagaccgtc ctgacgtgct ggtggccgct tgcctggcag ccatgaacgg cgtagaaatc    900
ggtgccctgc tgctgactgg cggttacgaa atggacgcgc gcatttctaa actgtgcgaa    960
cgtgctttcg ctaccggcct gccggtattt atggtgaaca ccaacacctg gcagacctct   1020
ctgagcctgc agagcttcaa cctggaagtt ccggttgacg atcacgaacg tatcgagaaa   1080
gttcaggaat acgttgctaa ctacatcaac gctgactgga tcgaatctct gactgccact   1140
tctgagcgca gccgtcgtct gtctccgcct gcgttccgtt atcagctgac tgaacttgcg   1200
cgcaaagcgg gcaaacgtat cgtactgccg gaaggtgacg aaccgcgtac cgttaaagca   1260
gccgctatct gtgctgaacg tggtatcgca acttgcgtac tgctgggtaa tccggcagag   1320
atcaaccgtg ttgcagcgtc tcagggtgta gaactgggtg cagggattga aatcgttgat   1380
ccagaagtgg ttcgcgaaag ctatgttggt cgtctggtcg aactgcgtaa gaacaaaggc   1440
atgaccgaaa ccgttgcccg cgaacagctg gaagacaacg tggtgctcgg tacgctgatg   1500
ctggaacagg atgaagttga tggtctggtt tccggtgctg ttcacactac cgcaaacacc   1560
atccgtccgc cgctgcagct gatcaaaact gcaccgggca gctccctggt atcttccgtg   1620
ttcttcatgc tgctgccgga acaggtttac gtttacggtg actgtgcgat caacccggat   1680
ccgaccgctg aacagctggc agaaatcgcg attcagtccg ctgattccgc tgcggccttc   1740
ggtatcgaac cgcgcgttgc tatgctctcc tactccaccg gtacttctgg tgcaggtagc   1800
gacgtagaaa aagttcgcga agcaactcgt ctggcgcagg aaaaacgtcc tgacctgatg   1860
atcgacggtc cgctgcagta cgacgctgcg gtaatggctg acgttgcgaa atccaaagcg   1920
ccgaactctc cggttgcagg tcgcgctacc gtgttcatct tcccggatct gaacaccggt   1980
aacaccacct acaaagcggt acagcgttct gccgacctga tctccatcgg ccgatgctg   2040
cagggtatgc gcaagccggt taacgacctg tcccgtggcg cactggttga cgatatcgtc   2100
tacaccatcg cgctgactgc gattcagtct gcacagcagc agtaa                   2145
```

<210> SEQ ID NO 3
<211> LENGTH: 1959
<212> TYPE: DNA
<213> ORGANISM: E. coli ATCC 27325

<400> SEQUENCE: 3

```
atgagccaaa ttcacaaaca caccattcct gccaacatcg cagaccgttg cctgataaac     60
cctcagcagt acgaggcgat gtatcaacaa tctattaacg tacctgatac cttctggggc    120
gaacagggaa aaattcttga ctggatcaaa ccttaccaga aggtgaaaaa cacctccttt    180
gcccccggta atgtgtccat taaatggtac gaggacggca cgctgaatct ggcggcaaac    240
tgccttgacc gccatctgca agaaaacggc gatcgtaccg ccatcatctg ggaaggcgac    300
gacgccagcc agagcaaaca tatcagctat aaagagctgc accgcgacgt ctgccgcttc    360
gccaataccc tgctcgagct gggcattaaa aaaggtgatg tggtggcgat ttatatgccg    420
```

```
atggtgccgg aagccgcggt tgcgatgctg gcctgcgccc gcattggcgc ggtgcattcg    480
gtgattttcg gcggcttctc gccggaagcc gttgccgggc gcattattga ttccaactca    540
cgactggtga tcacttccga cgaaggtgtg cgtgccgggc gcagtattcc gctgaagaaa    600
aacgttgatg acgcgctgaa aaacccgaac gtcaccagcg tagagcatgt ggtggtactg    660
aagcgtactg gcgggaaaat tgactggcag gaagggcgcg acctgtggtg gcacgacctg    720
gttgagcaag cgagcgatca gcaccaggcg aagagatga acgccgaaga tccgctgttt    780
attctctaca cctccggttc taccggtaag ccaaaaggtg tgctgcatac taccggcggt    840
tatctggtgt acgcggcgct gacctttaaa tatgtctttg attatcatcc gggtgatatc    900
tactggtgca ccgccgatgt gggctgggtg accggacaca gttacttgct gtacggcccg    960
ctggcctgcg gtgcgaccac gctgatgttt gaaggcgtac ccaactggcc gacgcctgcc   1020
cgtatggcgc aggtggtgga caagcatcag gtcaatattc tctataccgc acccacggcg   1080
atccgcgcgc tgatggcgga aggcgataaa gcgatcgaag caccgaccg ttcgtcgctg    1140
cgcattctcg gttccgtggg cgagccaatt aacccgaag cgtgggagtg gtactggaaa    1200
aaaatcggca acgagaaatg tccggtggtc gatacctggt ggcagaccga accggcggt     1260
ttcatgatca ccccgctgcc tggcgctacc gagctgaaag ccggttcggc aacacgtccg    1320
ttcttcggcg tgcaaccggc gctggtcgat aacgaaggta acccgctgga ggggccacc     1380
gaaggtagcc tggtaatcac cgactcctgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg gcgtgtggga cgacgtgctg    1560
aacgtctccg gtcaccgtct ggggacggca gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aaacccgctc cggcaaaatt atgcgccgta ttctgcgcaa aattgcggcg    1860
ggcgatacca gcaacctggg cgatacctcg acgcttgccg atcctggcgt agtcgagaag    1920
ctgcttgaag agaagcaggc tatcgcgatg ccatcgtaa                           1959

<210> SEQ ID NO 4
<211> LENGTH: 1284
<212> TYPE: DNA
<213> ORGANISM: E. coli ATCC 27325

<400> SEQUENCE: 4
atggctgata caaaagcaaa actcaccctc aacggggata cagctgttga actggatgtg     60
ctgaaaggca cgctgggtca agatgttatt gatatccgta ctctcggttc aaaaggtgtg    120
ttcacctttg acccaggctt cacttcaacc gcatcctgcg aatctaaaat tactttatt     180
gatggtgatg aaggtatttt gctgcaccgc ggtttcccga tcgatcagct ggcgaccgat    240
tctaactacc tggaagtttg ttacatcctg ctgaatggtg aaaaaccgac tcaggaacag    300
tatgacgaat ttaaaactac ggtgacccgt cataccatga tccacgagca gattacccgt    360
ctgttccatg ctttccgtcg cgactcgcat ccaatggcag tcatgtgtgg tattaccggc    420
gcgctggcgg cgttctatca cgactcgctg gatgttaaca atcctcgtca ccgtgaaatt    480
gccgcgttcc gcctgctgtc gaaaatgccg accatggccg cgatgtgtta caagtattcc    540
attggtcagc catttgttta cccgcgcaac gatctctcct acgccggtaa cttcctgaat    600
```

```
atgatgttct ccacgccgtg cgaaccgtat gaagttaatc cgattctgga acgtgctatg      660
gaccgtattc tgatcctgca cgctgaccat gaacagaacg cctctacctc caccgtgcgt      720
accgctggct cttcgggtgc gaacccgttt gcctgtatcg cagcaggtat tgcttcactg      780
tggggacctg cgcacggcgg tgctaacgaa gcggcgctga aatgctgga agaaatcagc       840 tccgttaaac acattccgga atttgttcgt cgtgcgaaag acaaaaatga ttctttccgc      900
ctgatgggct tcggtcaccg cgtgtacaaa aattacgacc cgcgcgccac cgtaatgcgt      960
gaaacctgcc atgaagtgct gaaagagctg ggcacgaagg atgacctgct ggaagtggct     1020
atggagctgg aaaacatcgc gctgaacgac ccgtacttta tcgagaagaa actgtacccg     1080
aacgtcgatt tctactctgg tatcatcctg aaagcgatgg gtattccgtc ttccatgttc     1140
accgtcattt tcgcaatggc acgtaccgtt ggctggatcg cccactggag cgaaatgcac     1200
agtgacggta tgaagattgc ccgtccgcgt cagctgtata caggatatga aaaacgcgac     1260
tttaaaagcg atatcaagcg ttaa                                            1284

<210> SEQ ID NO 5
<211> LENGTH: 2652
<212> TYPE: DNA
<213> ORGANISM: E. coli ATCC 27325

<400> SEQUENCE: 5
atgaacgaac aatattccgc attgcgtagt aatgtcagta tgctcggcaa agtgctggga       60
gaaaccatca aggatgcgtt gggagaaacac attcttgaac gcgtagaaac tatccgtaag     120
ttgtcgaaat cttcacgcgc tggcaatgat gctaaccgcc aggagttgct caccacctta     180
caaaatttgt cgaacgacga gctgctgccc gttgcgcgtg cgtttagtca gttcctgaac     240
ctggccaaca ccgccgagca ataccacagc attcgccga aaggcgaagc tgccagcaac      300
ccggaagtga tcgcccgcac cctgcgtaaa ctgaaaaacc agccggaact gagcgaagac     360
accatcaaaa aagcagtgga atcgctgtcg ctggaactgg tcctcacggc tcacccaacc     420
gaaattaccc gtcgtacact gatccacaaa atggtggaag tgaacgcctg tttaaaacag     480
ctcgataaca aagatatcgc tgactacgaa cacaaccagc tgatgcgtcg cctgcgccag     540
ttgatcgccc agtcatggca taccgatgaa atccgtaagc tgcgtccaag cccggtagat     600
gaagccaaat ggggctttgc cgtagtgaa acagcctgt ggcaaggcgt accaaattac        660
ctgcgcgaac tgaacgaaca actggaagag aacctcggct acaaactgcc cgtcgaattt     720
gttccggtcc gttttacttc gtggatgggc ggcgaccgcg acggcaaccc gaacgtcact     780
gccgatatca cccgccacgt cctgctactc agccgctgga agccaccga tttgttcctg       840 aaagatattc aggtgctggt ttctgaactg tcgatggttg aagcgacccc tgaactgctg     900
gcgctggttg gcgaagaagg tgccgcagaa ccgtatcgct atctgatgaa aaacctgcgt     960
tctcgcctga tggcgacaca ggcatggctg aagcgcgcc tgaaaggcga agaactgcca     1020
aaaccagaag gcctgctgac acaaaacgaa gaactgtggg aaccgctcta cgcttgctac     1080
cagtcacttc aggcgtgtgg catgggtatt atcgccaacg cgatctgct cgacaccctg     1140 cgccgcgtga atgtttcgg cgtaccgctg gtccgtattg atatccgtca ggagagcacg     1200
cgtcataccg aagcgctggg cgagctgacc cgctacctcg gtatcggcga ctacgaaagc     1260
tggtcagagg ccgacaaaca ggcgttcctg atccgcgaac tgaactccaa acgtccgctt     1320
ctgccgcgca actggcaacc aagcgccgaa acgcgcgaag tgctcgatac ctgccaggtg     1380
```

```
attgccgaag caccgcaagg ctccattgcc gcctacgtga tctcgatggc gaaaacgccg    1440
tccgacgtac tggctgtcca cctgctgctg aaagaagcgg gtatcgggtt tgcgatgccg    1500
gttgctccgc tgtttgaaac cctcgatgat ctgaacaacg ccaacgatgt catgacccag    1560
ctgctcaata ttgactggta tcgtggcctg attcagggca acagatggt gatgattggc     1620
tattccgact cagcaaaaga tgcgggagtg atggcagctt cctgggcgca atatcaggca    1680
caggatgcat taatcaaaac ctgcgaaaaa gcgggtattg agctgacgtt gttccacggt    1740
cgcggcggtt ccattggtcg cggcggcgca cctgctcatg cggcgctgct gtcacaaccg    1800
ccaggaagcc tgaaaggcgg cctgcgcgta accgaacagg gcgagatgat ccgctttaaa    1860
tatggtctgc agaaatcac cgtcagcagc ctgtcgcttt ataccggggc gattctggaa     1920
gccaacctgc tgccaccgcc ggagccgaaa gagagctggc gtcgcattat ggatgaactg    1980
tcagtcatct cctgcgatgt ctaccgcggc tacgtacgtg aaaacaaaga ttttgtgcct    2040
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acggcaaaca gagcgagctg gaggctatgt gccgcgattg gccattcttc    2280
tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaaagaagg ccaggaaccg    2580
gatcctcgcg tcgaacaagc gttaatggtc actattgccg ggattgcggc aggtatgcgt    2640
aataccggct aa                                                        2652
```

<210> SEQ ID NO 6
<211> LENGTH: 1203
<212> TYPE: DNA
<213> ORGANISM: E. coli ATCC 27325

<400> SEQUENCE: 6

```
atgtcgagta agttagtact ggttctgaac tgcggtagtt cttcactgaa atttgccatc     60
atcgatgcag taaatggtga agagtacctt tctggtttag ccgaatgttt ccacctgccc    120
gaagcacgta tcaaatggaa aatggacggc aataaacagg aagcggcttt aggtgcaggc    180
gccgctcaca gcgaagcgct caactttatc gttaatacta ttctggcaca aaaaccagaa    240
ctgtctcgcg agctgactgc tatcggtcac cgtatcgtac acggcggcga aaagtatacc    300
agctccgtag tgatcgatga gtctgttatt cagggtatca aagatgcagc ttcttttgca    360
ccgctgcaca acccggctca cctgatcggt atcgaagaag ctctgaaatc tttcccacag    420
ctgaaagaca aaaacgttgc tgtatttgac accgcgttcc accagactat gccggaagag    480
tcttacctct acgccctgcc ttacaacctg tacaagagc acggcatccg tcgttacggc    540
gcgcacggca ccagccactt ctatgtaacc caggaagcgg caaaaatgct gaacaaaccg    600
gtagaagaac tgaacatcat cacctgccac ctgggcaacg gtggttccgt ttctgctatc    660
cgcaacggta aatgcgttga cacctctatg ggcctgaccc cgctggaagg tctggtcatg    720
ggtacccgtt ctggtgatat cgatccggcg atcatcttcc acctgcacga caccctgggc    780
atgagcgttg acgcaatcaa caaactgctg accaaagagt ctggcctgct gggtctgacc    840
```

-continued

```
gaagtgacca gcgactgccg ctatgttgaa gacaactacg cgacgaaaga agacgcgaag    900
cgcgcaatgg acgtttactg ccaccgcctg gcgaaataca tcggtgccta cactgcgctg    960
atggatggtc gtctggacgc tgttgtattc actggtggta tcggtgaaaa tgccgcaatg   1020
gttcgtgaac tgtctctggg caaactgggc gtgctgggct ttgaagttga tcatgaacgc   1080
aacctggctg cacgtttcgg caaatctggt ttcatcaaca agaaggtac  ccgtcctgcg   1140 gtggttatcc caaccaacga agaactggtt atcgcgcaag acgcgagccg cctgactgcc   1200
tga                                                                 1203

<210> SEQ ID NO 7
<211> LENGTH: 21
<212> TYPE: DNA
<213> ORGANISM: Artificial Sequence
<220> FEATURE:
<223> OTHER INFORMATION: The sequence is synthesized.

<400> SEQUENCE: 7
tgggaagaaa ccacgaaact c                                              21

<210> SEQ ID NO 8
<211> LENGTH: 77
<212> TYPE: DNA
<213> ORGANISM: Artificial Sequence
<220> FEATURE:
<223> OTHER INFORMATION: The sequence is synthesized.

<400> SEQUENCE: 8
aattgttatc cgctcacaat tccacacatt atacgagccg gatgattaat tgtcaatgtt    60
tcagcaggta ggcgaga                                                   77

<210> SEQ ID NO 9
<211> LENGTH: 77
<212> TYPE: DNA
<213> ORGANISM: Artificial Sequence
<220> FEATURE:
<223> OTHER INFORMATION: The sequence is synthesized.

<400> SEQUENCE: 9
ctgggccttt cgttttatct gttgtttgtc ggtgaacgct ctcctgagta ggacaaataa    60
aacggtcgcc tggtacg                                                   77

<210> SEQ ID NO 10
<211> LENGTH: 19
<212> TYPE: DNA
<213> ORGANISM: Artificial Sequence
<220> FEATURE:
<223> OTHER INFORMATION: The sequence is synthesized.

<400> SEQUENCE: 10
ttatccgccg acattgctg                                                 19

<210> SEQ ID NO 11
<211> LENGTH: 85
<212> TYPE: DNA
<213> ORGANISM: Artificial Sequence
<220> FEATURE:
<223> OTHER INFORMATION: The sequence is synthesized.
```

```
<400> SEQUENCE: 11
tccggctcgt ataatgtgtg gaattgtgag cggataacaa tttcacacag gaaacagacc    60
atgacctctc cggttatcgg taccc                                          85

<210> SEQ ID NO 12
<211> LENGTH: 79
<212> TYPE: DNA
<213> ORGANISM: Artificial Sequence
<220> FEATURE:
<223> OTHER INFORMATION: The sequence is synthesized.

<400> SEQUENCE: 12
acaaacaaca gataaaacga aaggcccagt ctttcgactg agcctttcgt tttatttgtc    60
attcgttgtc acccgcggt                                                 79

<210> SEQ ID NO 13
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 13
agtcctaggt ataatactag ttatcattcc ccacactacg ggttttagag ctagaa        56

<210> SEQ ID NO 14
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 14
ttctagctct aaaacccccc gtagtgtggg gaatgactag tattatacct aggact        56

<210> SEQ ID NO 15
<211> LENGTH: 25
<212> TYPE: DNA
<213> ORGANISM: Artificial Sequence
<220> FEATURE:
<223> OTHER INFORMATION: The sequence is synthesized.

<400> SEQUENCE: 15
aatagttgtt gccgcctgag taact                                          25

<210> SEQ ID NO 16
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 16
aattgttatc cgctcacaat tccacacatt atacgagccg gatgattaat tgtcaagcag    60
ccagtaatct tccatccctt t                                              81

<210> SEQ ID NO 17
<211> LENGTH: 85
<212> TYPE: DNA
<213> ORGANISM: Artificial Sequence
<220> FEATURE:
<223> OTHER INFORMATION: The sequence is synthesized.
```

```
<400> SEQUENCE: 17
aaagactggg cctttcgttt tatctgttgt ttgtcggtga acgctctcct gagtaggaca    60
aatatcggat tcgcaccgga agaga                                         85

<210> SEQ ID NO 18
<211> LENGTH: 22
<212> TYPE: DNA
<213> ORGANISM: Artificial Sequence
<220> FEATURE:
<223> OTHER INFORMATION: The sequence is synthesized.

<400> SEQUENCE: 18
tgtcccgtgc cagaagatga gg                                            22

<210> SEQ ID NO 19
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 19
tccggctcgt ataatgtgtg gaattgtgag cggataacaa tttcacacag gaaacagacc    60
gtgtcccgta ttattatgct g                                             81

<210> SEQ ID NO 20
<211> LENGTH: 84
<212> TYPE: DNA
<213> ORGANISM: Artificial Sequence
<220> FEATURE:
<223> OTHER INFORMATION: The sequence is synthesized.

<400> SEQUENCE: 20
caccgacaaa caacagataa aacgaaaggc ccagtctttc gactgagcct ttcgttttat    60
ttgttactgc tgctgtgcag actg                                          84

<210> SEQ ID NO 21
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 21
agtcctaggt ataatactag tagggattat gaacggcaat ggttttagag ctagaa        56

<210> SEQ ID NO 22
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 22
ttctagctct aaaaccattg ccgttcataa tccctactag tattatacct aggact        56

<210> SEQ ID NO 23
<211> LENGTH: 22
<212> TYPE: DNA
<213> ORGANISM: Artificial Sequence
<220> FEATURE:
<223> OTHER INFORMATION: The sequence is synthesized.
```

<400> SEQUENCE: 23
ggcgattgct actgctgatg ct                                              22

<210> SEQ ID NO 24
<211> LENGTH: 78
<212> TYPE: DNA
<213> ORGANISM: Artificial Sequence
<220> FEATURE:
<223> OTHER INFORMATION: The sequence is synthesized.

<400> SEQUENCE: 24
aattgttatc cgctcacaat tccacacatt atacgagccg gatgattaat tgtcaaccca    60
atactgggcg aagggaga                                                  78

<210> SEQ ID NO 25
<211> LENGTH: 85
<212> TYPE: DNA
<213> ORGANISM: Artificial Sequence
<220> FEATURE:
<223> OTHER INFORMATION: The sequence is synthesized.

<400> SEQUENCE: 25
aaagactggg cctttcgttt tatctgttgt tgtcggtga acgctctcct gagtaggaca    60
aatcgctgcc aaggactctg aggat                                         85

<210> SEQ ID NO 26
<211> LENGTH: 22
<212> TYPE: DNA
<213> ORGANISM: Artificial Sequence
<220> FEATURE:
<223> OTHER INFORMATION: The sequence is synthesized.

<400> SEQUENCE: 26
tagggcattg ggagggcgat tt                                              22

<210> SEQ ID NO 27
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 27
tccggctcgt ataatgtgtg gaattgtgag cggataacaa tttcacacag gaaacagacc    60
atgagccaaa ttcacaaaca c                                              81

<210> SEQ ID NO 28
<211> LENGTH: 84
<212> TYPE: DNA
<213> ORGANISM: Artificial Sequence
<220> FEATURE:
<223> OTHER INFORMATION: The sequence is synthesized.

<400> SEQUENCE: 28
caccgacaaa caacagataa acgaaaggc ccagtctttc gactgagcct ttcgttttat     60
ttgttacgat ggcatcgcga tagc                                           84

<210> SEQ ID NO 29
<211> LENGTH: 56
<212> TYPE: DNA
<213> ORGANISM: Artificial Sequence
<220> FEATURE:

<223> OTHER INFORMATION: The sequence is synthesized.

<400> SEQUENCE: 29
agtcctaggt ataatactag tcattaccac ttatggcgaa cgttttagag ctagaa    56

<210> SEQ ID NO 30
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 30
ttctagctct aaaacgttcg ccataagtgg taatgactag tattatacct aggact    56

<210> SEQ ID NO 31
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 31
acccaacctt acgcaaccag    20

<210> SEQ ID NO 32
<211> LENGTH: 76
<212> TYPE: DNA
<213> ORGANISM: Artificial Sequence
<220> FEATURE:
<223> OTHER INFORMATION: The sequence is synthesized.

<400> SEQUENCE: 32
aattgttatc cgctcacaat tccacacatt atacgagccg gatgattaat tgtcaattgt    60
tcgataaccg cagcat    76

<210> SEQ ID NO 33
<211> LENGTH: 80
<212> TYPE: DNA
<213> ORGANISM: Artificial Sequence
<220> FEATURE:
<223> OTHER INFORMATION: The sequence is synthesized.

<400> SEQUENCE: 33
aaagactggg cctttcgttt tatctgttgt ttgtcggtga acgctctcct gagtaggaca    60
aatcgctggc gtgctttgaa    80

<210> SEQ ID NO 34
<211> LENGTH: 19
<212> TYPE: DNA
<213> ORGANISM: Artificial Sequence
<220> FEATURE:
<223> OTHER INFORMATION: The sequence is synthesized.

<400> SEQUENCE: 34
ggcgtaactc agcaggcag    19

<210> SEQ ID NO 35
<211> LENGTH: 84
<212> TYPE: DNA
<213> ORGANISM: Artificial Sequence
<220> FEATURE:
<223> OTHER INFORMATION: The sequence is synthesized.

<400> SEQUENCE: 35
tccggctcgt ataatgtgtg gaattgtgag cggataacaa tttcacacag gaaacagacc    60
atggctgata caaaagcaaa actc    84

<210> SEQ ID NO 36
<211> LENGTH: 88
<212> TYPE: DNA
<213> ORGANISM: Artificial Sequence
<220> FEATURE:
<223> OTHER INFORMATION: The sequence is synthesized.

<400> SEQUENCE: 36
caccgacaaa caacagataa aacgaaaggc ccagtctttc gactgagcct ttcgttttat    60
ttgttaacgc ttgatatcgc ttttaaag    88

<210> SEQ ID NO 37
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 37
agtcctaggt ataatactag tacactggct ggatgtgcaa cgttttagag ctagaa    56

<210> SEQ ID NO 38
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 38
ttctagctct aaaacgttgc acatccagcc agtgtactag tattatacct aggact    56

<210> SEQ ID NO 39
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 39
ttcatcggga cgagtggaga    20

<210> SEQ ID NO 40
<211> LENGTH: 76
<212> TYPE: DNA
<213> ORGANISM: Artificial Sequence
<220> FEATURE:
<223> OTHER INFORMATION: The sequence is synthesized.

<400> SEQUENCE: 40
aattgttatc cgctcacaat tccacacatt atacgagccg gatgattaat tgtcaaccat    60
agcatcgcca atctga    76

<210> SEQ ID NO 41
<211> LENGTH: 80
<212> TYPE: DNA
<213> ORGANISM: Artificial Sequence
<220> FEATURE:
<223> OTHER INFORMATION: The sequence is synthesized.

<400> SEQUENCE: 41
ctgggccttt cgttttatct gttgtttgtc ggtgaacgct ctcctgagta ggacaaatac       60
ccaaaggtga agataaagcc                                                  80

<210> SEQ ID NO 42
<211> LENGTH: 24
<212> TYPE: DNA
<213> ORGANISM: Artificial Sequence
<220> FEATURE:
<223> OTHER INFORMATION: The sequence is synthesized.

<400> SEQUENCE: 42
cattccctct acagaactag ccct                                             24

<210> SEQ ID NO 43
<211> LENGTH: 82
<212> TYPE: DNA
<213> ORGANISM: Artificial Sequence
<220> FEATURE:
<223> OTHER INFORMATION: The sequence is synthesized.

<400> SEQUENCE: 43
tccggctcgt ataatgtgtg gaattgtgag cggataacaa tttcacacag gaaacagacc       60
atgaacgaac aatattccgc at                                               82

<210> SEQ ID NO 44
<211> LENGTH: 80
<212> TYPE: DNA
<213> ORGANISM: Artificial Sequence
<220> FEATURE:
<223> OTHER INFORMATION: The sequence is synthesized.

<400> SEQUENCE: 44
acaaacaaca gataaaacga aaggcccagt ctttcgactg agcctttcgt tttatttgtt       60
agccggtatt acgcatacct                                                  80

<210> SEQ ID NO 45
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 45
agtcctaggt ataatactag taacacagca atacggtacg cgttttagag ctagaa          56

<210> SEQ ID NO 46
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 46
ttctagctct aaaacgcgta ccgtattgct gtgttactag tattatacct aggact          56

<210> SEQ ID NO 47
<211> LENGTH: 22
<212> TYPE: DNA
<213> ORGANISM: Artificial Sequence
<220> FEATURE:
<223> OTHER INFORMATION: The sequence is synthesized.

```
<400> SEQUENCE: 47
actggttctg aactgcggta gt                                                22

<210> SEQ ID NO 48
<211> LENGTH: 22
<212> TYPE: DNA
<213> ORGANISM: Artificial sequence
<220> FEATURE:
<223> OTHER INFORMATION: The sequence is synthesized.

<400> SEQUENCE: 48
tgtaaggcag ggcgtagagg ta                                                22

<210> SEQ ID NO 49
<211> LENGTH: 21
<212> TYPE: DNA
<213> ORGANISM: Artificial Sequence
<220> FEATURE:
<223> OTHER INFORMATION: The sequence is synthesized.

<400> SEQUENCE: 49
aatgccgcaa tggttcgtga a                                                 21

<210> SEQ ID NO 50
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 50
gccgtcgtgg tggaagagtt                                                   20

<210> SEQ ID NO 51
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 51
agtcctaggt ataatactag tctttctatgt aacccaggaa ggttttagag ctagaa          56

<210> SEQ ID NO 52
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 52
ttctagctct aaaaccttcc tgggttacat agaagactag tattatacct aggact           56

<210> SEQ ID NO 53
<211> LENGTH: 74
<212> TYPE: DNA
<213> ORGANISM: Artificial Sequence
<220> FEATURE:
<223> OTHER INFORMATION: The sequence is synthesized.

<400> SEQUENCE: 53
ttgacaatta atcatccggc tcgtataatg tgtggaattg tgagcggata acaatttcac       60
acaggaaaca gacc                                                         74
```

GENETICALLY ENGINEERED BACTERIUM OF *ESCHERICHIA COLI* AND METHOD FOR FERMENTATION PRODUCTION OF L-THEANINE THEREOF

CROSS REFERENCE TO THE RELATED APPLICATIONS

This application is based upon and claims priority to Chinese Patent Application No. 202111159099.6, filed on Sep. 30, 2021, the entire contents of which are incorporated herein by reference.

REFERENCE TO SEQUENCE LISTING

The Sequence Listing is submitted concurrently with the specification as an ASCII formatted text file via EFS-Web, with a file name of "Sequence_listing.TXT", a creation date of Dec. 30, 2021, and a size of 27,472 bytes. The Sequence Listing filed via EFS-Web is part of the specification and is incorporated in its entirety by reference herein.

FIELD OF TECHNOLOGY

The present disclosure belongs to the bioengineering field, and specifically relates to a method for fermentation production of L-theanine by using a genetically engineered bacterium of *Escherichia coli*.

BACKGROUND

L-theanine (N-ethyl-γ-L-glutamine) is a kind of particular nonprotein amino acid in tea leaves. L-theanine was isolated from Jade Leaf Tea and named by a Japanese scholar, Mijiro Mito in 1950. L-theanine is mainly present in tea plants and exists in a free form; L-theanine does not participate in protein synthesis and accounts for 40%-70% of the total amount of free amino acids in vivo. L-theanine has a leaching rate of 80% in tea water and is a major component to make tea water fresh and refreshing, and has a positive correlation coefficient of 0.787-0.876 with the grade of green tea, and is also an important substance to evaluate the quality and flavor of other teas. With the in-depth studies on physiological activity of L-theanine, L-theanine has extensive application prospect in the fields of food, health and medicine.

At present, the food-grade L-theanine is obtained by microbial synthesis. CN103409475B has reported a gene of γ-glutamyl transpeptidase obtained by artificial synthesis, where *Escherichia coli* is used as a host bacterium to construct a genetically engineered bacterium overexpressing γ-glutamyl transpeptidase; the recombinase acts on different concentrations of glutamine and ethylamine hydrochloride to obtain L-theanine. CN104087535B has reported that a cell is prepared with *Pseudomonas nitroreducens* NTLC4.002 (accession number: CCTCC M2014254) as an original strain to transform glutamine and ethylamine to produce L-theanine. CN106893748B has reported that L-theanine is synthesized with γ-glutamylmethylamide synthetase and phosphokinase as catalysts and with sodium L-glutamate, ethylamine hydrochloride and a small amount of ATP as substrates. CN 102719367B has reported that a γ-glutamylmethylamide synthetase is produced by *Sporidiobolus pararoseus* screened from rhizosphere soil of a tea tree, then the enzyme catalyzes sodium L-glutamate, ethylamine hydrochloride and ATP to produce L-theanine. The major problem of L-theanine enzymatic synthesis via microorganisms lies in the higher price of raw materials of glutamine, glutamate and ATP. Therefore, the production cost is very high and the product is hardly applied in large scale.

The methods of preparing L-theanine with glucose as a raw material via microbial fermentation (CN109370966B and CN109777763B) are featured by simple and easy-to-get raw materials, simple production links and lower cost. But the production of L-theanine via fermentation has lots of problems, such as, low titer, lower yield and more by-products. Moreover, ethylamine has an inhibiting effect on microbial growth to cause decreased cell concentration and partial cell autolysis during fermentation, thereby leading to complex components of fermentation broth and difficulties in product extraction.

In the aspect of theanine separation and extraction, CN105061249B has disclosed that macromolecular substances in liquid waste are removed by ultrafiltration, then basic cupric carbonate and dilute sulphuric acid are added and reacted to generate theanine-copper sulfate, and then copper ions and sulphate ions in the theanine-copper sulfate are removed by electrodialysis, then water in the fresh water chamber is removed by concentration under reduced pressure, and sulfuric acid is separated from the sulfuric acid-theanine with absolute ethanol. CN109851520A has disclosed that L-theanine is obtained by performing ultrafiltration, decoloration, concentration, crystallization and other steps after adding a flocculant and an ion remover to the L-theanine reaction solution. A large number of acid/base reagents or flocculants are used in the above methods; yield and product purity are low. Therefore, it is also urgent to provide a separation and purification method of high-purity L-theanine.

SUMMARY

The object of the present invention is to obtain a genetically engineered bacterium for producing L-theanine with high yield and stable production performance, and to provide a fermentation method, and a purification method thereof.

Directed to the above existing problems, the technical solutions of the present invention are as follows:

The first technical solution of the present invention is a plasmid-free genetically engineered bacterium for the efficient L-theanine fermentation with glucose and other cheap carbon sources as substrates. With a genetically engineered bacterium producing L-theanine constructed via Chinese invention patent ZL 201811215068.6 (CN 109370966 B) as an original strain, the genetically engineered bacterium of this present invention is obtained by the following modification: integrating a fructose 6-phosphate phosphoketolase gene xfp, a phosphoacetyl transferase gene pta, an acetyl-CoA synthetase gene acs, a citrate synthase gene gltA, and a phosphoenolpyruvate carboxylase gene ppc on the genome, and knocking out an acetokinase gene ackA.

In further embodiments, the fructose 6-phosphate phosphoketolase gene xfp is derived from *Bifidobacterium adolescentis* ATCC 15703 and has a nucleotide sequence as shown in SEQ ID NO:1.

In further embodiments, the phosphoacetyl transferase gene pta is derived from *Escherichia coli* ATCC 27325 and has a nucleotide sequence as shown in SEQ ID NO:2.

In further embodiments, the acetyl-CoA synthetase gene acs is derived from *Escherichia coli* ATCC 27325 has a nucleotide sequence as shown in SEQ ID NO:3.

In further embodiments the citrate synthase gene gltA is derived from *Escherichia coli* ATCC 27325 and has a nucleotide sequence as shown in SEQ ID NO:4.

In further embodiments, the phosphoenolpyruvate carboxylase gene ppc is derived from *Escherichia coli* ATCC 27325 and has a nucleotide sequence as shown in SEQ ID NO:5.

In further embodiments, the acetokinase gene ackA has a nucleotide sequence as shown in SEQ ID NO:6.

In further embodiments, the genes xfp, pta, acs, gltA, and ppc are respectively controlled by a trc promoter; promoters of these genes are all the trc promoter.

The genetically engineered bacterium producing L-theanine constructed via Chinese invention patent ZL 201811215068.6 is obtained by integrating a single copy of a RNA polymerase gene T7RNAP which is derived from a T7 phage and controlled by a xylose promoter, a dual copy of a γ-glutamylmethylamide synthetase gene gmas which is derived from *Methylovorus mays* and controlled by a T7 promoter on the genome of *Escherichia coli* W3110, knocking out a xylose operon transcription factor gene xylR and knocking out a succinyl CoA synthetase gene sucCD.

The second technical solution of the present invention is a construction method of the above genetically engineered bacterium; a CRISPR/Cas 9 mediated gene editing technology is used for directional modification on the genome of *Escherichia coli*, and specifically including the following steps:

(1) to enhance carbon cycle and reduce carbon source loss, a single copy of the fructose 6-phosphate phosphoketolase gene xfp (as shown in SEQ ID NO:1) derived from *Bifidobacterium adolescentis* ATCC 15703 is integrated on a site gapC of the original strain genome;

(2) to enhance the metabolism of acetyl phosphate to acetyl-CoA, a single copy of the phosphoacetyl transferase gene pta (as shown in SEQ ID NO:2) derived from *Escherichia coli* ATCC 27325 is integrated on a site yjiT of the original strain genome;

(3) to enhance the metabolism of acetic acid to an acetyl-CoA, a single copy of the acetyl-CoA synthetase gene acs (as shown in SEQ ID NO:3) derived from *Escherichia coli* ATCC 27325 is integrated on a site yghE of the original strain genome;

(4) to enhance the metabolism of acetyl-CoA to citric acid, a single copy of the citrate synthase gene gltA (as shown in SEQ ID NO:4) derived from *Escherichia coli* ATCC 27325 is integrated on a site ylbE of the original strain genome;

(5) to enhance the metabolism of phosphoenolpyruvic acid to oxaloacetic acid, a single copy of the phosphoenolpyruvate carboxylase gene ppc (as shown in SEQ ID NO:5) derived from *Escherichia coli* ATCC 27325 is integrated on a site yeeL of the original strain genome;

(6) to reduce the accumulation of acetic acid, the acetokinase gene ackA (as shown in SEQ ID NO:6) is knocked out of the original strain genome.

There is no precedence order among the above construction steps (1)-(6), and the order may be adjusted according to the requirements. The final genetically engineered bacterium is named *E. coli* THEE.

The third technical solution of the present invention is an application of the above genetically engineered bacterium, especially in production of L-theanine via a fermentation method.

In further embodiments, the fermentation method for producing L-theanine using the above genetically engineered bacterium *E. coli* THEE is specifically as follows:

Fermentation cultivation: inoculating a seed solution into a fresh fermentation medium by 10-15% inoculum size, where a pH value is controlled within 6.7-7.2 during the fermentation, a temperature is maintained within 28-36° C., and a dissolved oxygen is within 10-30%; adding a glucose solution by a fed-batch way to maintain a glucose concentration in the fermentation medium less than 1 g/L after glucose in the medium is completely consumed.

In further embodiments, adding 600 g/L glucose solution by a fed-batch way to maintain a glucose concentration in the fermentation medium less than 1 g/L.

In further embodiments, in order to reduce the influence of ethylamine on the growth of bacteria, an OD-linked ethylamine supplementary strategy is taken in the fermentation process; when $OD_{600\ nm}$ is above 8-12, addition of ethylamine is started, and an ethylamine fed-batch rate is adjusted for once every 0.8-1.2 h; the ethylamine fed-batch rate $(g \cdot L^{-1} \cdot h^{-1}) = 0.5 \times OD_{600\ nm}$ value/(fermentation volume (L)×fermentation time (h)).

After the fermentation is performed in a 5 L fermentation tank for 20-25 h, L-theanine has a titer of 75-80 g/L and a yield of 52-55%.

In further embodiments, the seed culture method is as follows: taking a proper amount of sterile water to an eggplant-shaped flask, and inoculating a bacterial suspension into a seed medium, stabilizing a pH value around 7.0, and keeping a temperature of 37° C. and dissolved oxygen within 25-35%, and culturing to a dry cell weight of 5-6 g/L.

In further embodiments, a slant culture method is as follows: scratching a loop of bacterium from a bacterial tube in a −80° C. refrigerator, evenly coating on an activated slant, culturing for 12-16 h at 37° C., and transferring to the eggplant-shaped flask for continuous culture for 12-16 h.

In further embodiments, the slant medium consists of: 1-5 g/L glucose, 5-10 g/L peptone, 5-10 g/L beef extract, 1-5 g/L yeast powder, 1-2.5 g/L sodium chloride, and 15-20 g/L agar with a pH of 7.0-7.2.

In further embodiments, the seed medium consists of: 20-30 g/L glucose, 5-10 g/L yeast extract, 10-20 g/L peptone, 10-20 g/L sodium chloride, and the rest is water, where a pH value is 7.0-7.2.

In further embodiments, the fermentation medium consists of: 10-40 g/L glucose, 2-8 g/L yeast powder, 2-20 ml/L corn syrup, 0.2-2.0 g/L citric acid, 0.5-3.2 g/L monopotassium phosphate, 0.5-2.4 g/L dipotassium phosphate, 0.2-1.2 g/L magnesium sulfate, and the rest is water, wherein a pH value is 7.0-7.2.

The fourth technical solution of the present invention is a method for separation and extraction of L-theanine from the above fermentation broth, specifically as follows:

(1) heating up the L-theanine fermentation broth to 55-60° C. and maintaining for 20-30 min, and cooling to 35-40° C., performing microfiltration with a 50-70 nm ceramic membrane for sterilization and collecting a filtrate, and supplementing water in 0.5-1 times the volume of the fermentation broth when the filtrate has a flow rate lower than 5 mL/min at a pressure of 0.2-0.3 Mpa, and when L-theanine has a concentration less than 2 g/L in a retentate solution, the microfiltration of ceramic membrane is over.

(2) making the ceramic membrane filtrate flowing through a cationic resin to absorb the L-theanine, performing elution and collection with ammonia water having a mass fraction of 0.5%-1%; making an eluent flowing through an anion resin to absorb pigments, and collecting a resin effluent.

In further embodiments, the cationic resin is a 001×7 styrene series strong acidic cation-exchange resin.

In further embodiments, the anion resin is a D213 acrylic acid series strong alkali anion-exchange resin.

(3) pumping the resin effluent into a decoloring tank, adding a pharmaceutical activated carbon with 1%-3% mass of the L-theanine for decolorization until a feed liquid has a light transmittance above 96%, pumping a decoloring solution into an evaporator, and performing concentration under reduced pressure until a volume concentration times of 6-9 is achieved.

In further embodiments, a vacuum degree of −0.08 MPa and a temperature of 60° C. are maintained during the concentration under reduced pressure.

(4) pumping a concentrated solution into a crystallizer, and adding ethanol with 30%-50% volume of the concentrated solution, performing vacuum cooling crystallization and centrifugal separation to collect a wet crystal, and drying the crystal to obtain the L-theanine final product.

The beneficial effects of the present invention are:

(1) Pyruvate dehydrogenase catalyzes pyruvic acid to form acetyl-CoA and $CO_2$, therefore, *Escherichia coli* transforms a molecule of glucose into two molecules of acetyl-CoA via glycolytic pathway at most, and the remainder is lost in a form of $CO_2$, which seriously limits the conversion rate of glucose into L-theanine. The present invention may transform a molecule of glucose into three molecules of acetyl-CoA at most by introducing fructose 6-phosphate phosphoketolase. The fructose 6-phosphate phosphoketolase gene is integrated on an *Escherichia coli* genome to construct a metabolic pathway from fructose-6-phosphate and xylolose 5-phosphate to acetyl phosphate, and the expression of an endogenous phosphoacetyl transferase is enhanced such that acetyl phosphate is transformed into acetyl-CoA. The above metabolic modification strategy may effectively reduce the metabolism of pyruvic acid to acetyl-CoA, thus reducing carbon loss and improving the conversion rate of glucose into L-theanine.

(2) A certain amount of by-product acetic acid will be produced during the fermentation of *Escherichia coli*, which affect the normal growth of the bacterial cell. Excessive synthesis of acetyl phosphate will further intensify the accumulation of acetic acid. To reduce the content of the by-product acetic acid, the present invention knocks out acetokinase to block the metabolism of acetyl phosphate to acetic acid, and the expression of the endogenous acetyl-CoA synthetase gene is enhanced to transform acetic acid into acetyl-CoA. The above metabolic modification strategy may effectively reduce the inhibition of acetic acid on cell growth, thus promoting the L-theanine production rate of per unit of bacterial cell.

(3) The introduction of a heterolactic fermentation will result in the accumulation of triphosphate glyceraldehyde and acetyl-CoA. To enhance the metabolic flux of tricarboxylic acid cycle, the present invention reinforces the expression of the endogenesis citrate synthase and phosphoenolpyruvate carboxylase, which provides enough enzymes and substrates oxaloacetic acid for the initial reaction of tricarboxylic acid cycle, namely, the synthesis of citric acid.

(4) Ethylamine is a precursor of L-theanine during the fermentation; but a large number of ethylamine will cause strong toxic action on bacterial cells. A strategy of fed-batch ethylamine at a constant speed is used in the fermentation process to effectively control the concentration of ethylamine in the fermentation broth, but the bacterial cell requires different consumption of ethylamine in different growth stages, and constant feeding will affect the L-theanine producing ability of the bacterial cells. Based on the tolerance degree of the bacterial cell on ethylamine in different growth stages, the present invention develops an OD-linked ethylamine feeding technique to make the fed-batch rate of ethylamine coupled to the bacterial biomass, thus fitting an empirical equation, such that the bacterial cells may metabolize ethylamine to produce L-theanine to the maximum extent, thereby significantly increasing the biomass and L-theanine yield.

(5) The present invention uses membrane separation in combination with a cation-anion resin series technique instead of an L-theanine extraction and purification technique by a conventional method of precipitation to decrease the use of activated carbon, which improves the product yield and product quality. Moreover, the one-step crystallization yield is 72.3% and the L-theanine final product has a purity of 99%. The present invention may achieve qualified products only through one-step crystallization without a refining step, which shortens a purification route, reduces pollution risk and increases the production stability.

DESCRIPTION OF THE EMBODIMENTS

To understand the object, technical solution and advantages more clearly, the present invention will be further described in detail with reference to detailed examples. It should be understood that detailed examples described herein are merely used to explain the present invention, but not constructed as limiting thereto.

In the present invention, the genetically engineered bacterium producing L-theanine constructed via Chinese invention patent ZL 201811215068.6 (CN 109370966 B) serves as an original strain. The original strain is obtained by the following steps: integrating a single copy of a RNA polymerase gene T7RNAP which is derived from a T7 phage and has a nucleotide sequence as shown in SEQ ID NO:1 of CN 109370966 B on a site lacI-lacZ of the *Escherichia coli* W3110 genome and controlled by a xylose promoter $P_{xylF}$, integrating a dual copy of γ-glutamylmethylamide synthetase gene gmas which is derived from *Methylovorus mays* and has a nucleotide sequence as shown in SEQ ID NO:2 of CN 109370966 B on sites yghX and yeeP of the W3110 genome, optimized via a codon and controlled by a T7 promoter, knocking out a xylose operon transcription factor gene xylR of the W3110, and knocking out a succinyl-CoA synthetase gene sucCD of the W3110. Detailed construction process may be referring to CN 109370966 B.

The trc promoter sequence used in the present invention is as follows:

```
                                (as shown in SEQ ID NO: 53)
TTGACAATTAATCATCCGGCTCGTATAATGTGTGGAATTGTGAGCGGATA

ACAATTTCACACAGGAAACAGACC.
```

In examples of the present invention, sequences of the genes xfp, pta, acs, gltA, ppc and ackA involved in the construction process of the *E. coli* THEE are shown in the SEQ ID NO:1-6.

The present invention will be further explained by detailed embodiments with reference to the accompanying drawings.

Figure 1:
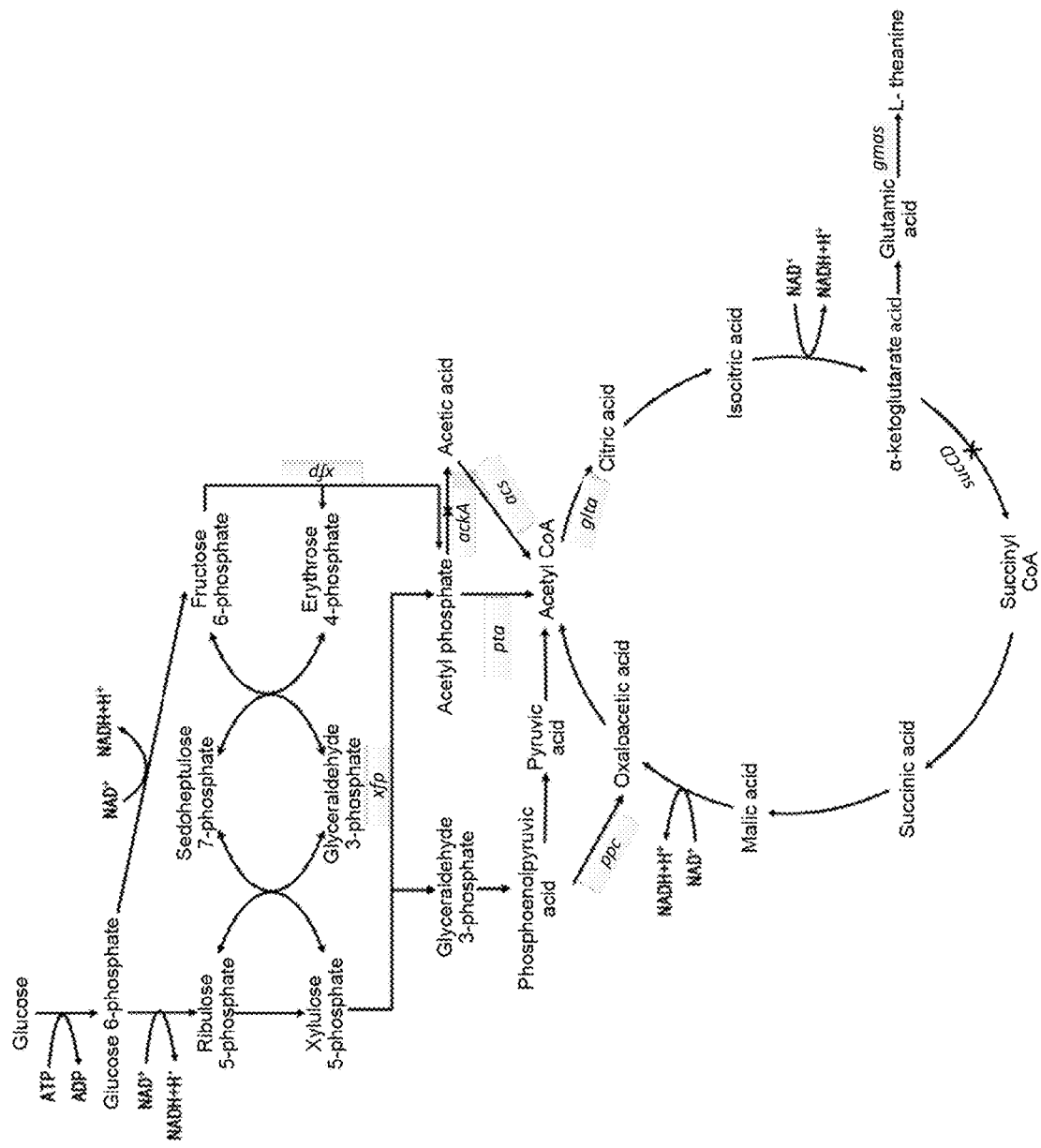
FIG. 1 is a metabolic modification strategy diagram of a genetically engineered bacterium *Escherichia coli* THEE where, the gray filling gene is a modification site of the present invention.

Example 1: Construction of a Genetically Engineered Bacterium *E. coli* THEE (Metabolic Modification Strategy is Shown in FIG. 1)

1. Gene Editing Method

The present invention is implemented by using a CRISPR/Cas 9-mediated gene editing method and by reference to the literature (Metabolic Engineering, 2015, 31: 13-21), and two plasmids used in the method are respectively pGRB and pREDCas9. pREDCas9 carried a gRNA plasmid elimination system, a Red recombination system of λ phage and a Cas9 protein expression system with miramycin resistance (working concentration: 100 mg/L), and was cultured at 32° C.; a pGRB plasmid with a framework of pUC18 included a promoter J23100, a gRNA-Cas9 binding domain sequence and terminator sequence with ampicillin resistance (working concentration: 100 mg/L) was cultured at 37° C.

2. Specific Construction Process of the Strain

Figure 2:
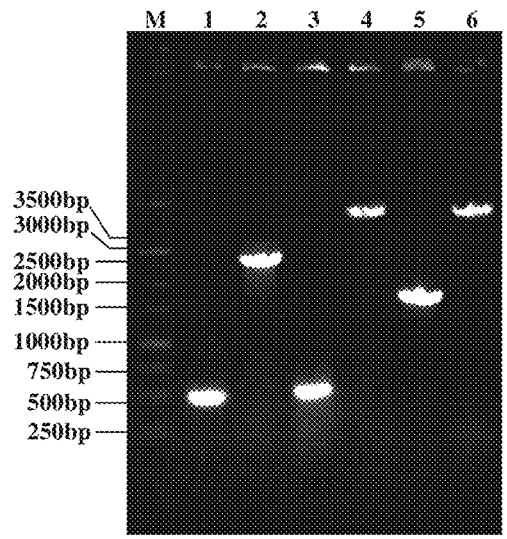
FIG. 2 is an electrophoretogram of gapC::$P_{trc}$-xfp integration where, M denotes a 1 kb Maker; 1 denotes an upstream homologous arm; 2 denotes a target gene; 3 denotes a downstream homologous arm; 4 denotes an overlapped fragment; 5 denotes a PCR fragment of the original strain; and 6 denotes a PCR fragment of the target strain.

The genetically engineered bacterium producing L-theanine constructed via Chinese invention patent ZL 201811215068.6 served as an original strain. The original strain was obtained by the following steps: performing a single copy of a RNA polymerase gene T7RNAP which was derived from a T7 phage and had a nucleotide sequence as shown in SEQ ID NO:1 of CN 109370966 B on a site lacI-lacZ of the *Escherichia coli* genome and controlled by a xylose promoter $P_{xylF}$, performing a dual copy of γ-glutamylmethylamide synthetase gene gmas which had a nucleotide sequence as shown in SEQ ID NO:2 of CN 109370966 B on sites yghX and yeeP of the genome, optimized via a codon and controlled by a T7 promoter, knocking out a xylose operon transcription factor gene xylR, and knocking out a succinyl-CoA synthetase gene sucCD of the W3110, and modified as follows:

2.1 Integration of $P_{trc}$-xfp (a Fragment Containing a trc Promoter and xfp Gene) on a Pseudogene gapC Site Using the *E. coli* ATCC27325 genome as a template, upstream homologous arm primers UP-gapC-S (SEQ ID NO:7), UP-gapC-A (SEQ ID NO:8) and downstream homologous arm primers DN-gapC-S (SEQ ID NO:9), DN-gapC-A (SEQ ID NO:10) were designed according to the upstream and downstream sequences of the gene gapC, the upstream and downstream homologous arms of the gene gapC were amplified; primers xfp-S (SEQ ID NO:11), xfp-A (SEQ ID NO:12) were designed according to the gene xfp, and the xfp gene fragment was amplified. The promoter $P_{trc}$ was designed in the reverse primer of upstream homologous arm of gapC gene and forward primer of the xfp gene. The above fragments were subjected to PCR overlapping to obtain an integrated fragment of the gene xfp (upstream homologous arm of gene gapC-$P_{trc}$-xfp-downstream homologous arm of gene gapC); the DNA fragment containing a target sequence for pGRB-gapC construction was prepared by annealing primers gRNA-gapC-S (SEQ ID NO:13) and gRNA-gapC-A (SEQ ID NO:14), then the DNA fragment was recombined with a linearized pGRB vector to obtain a recombinant pGRB-gapC. The integrated fragment and pGRB-gapC were electro-transformed into competent cells of an *Escherichia coli* original strain containing a pREDCas9 vector, then the electro-transformed bacterial cells after being resuscitatively cultured were coated on a LB plate containing ampicillin and miramycin, and cultured overnight at 32° C., then a positive recombinant was verified by PCR, and then, the pGRB-gapC for gene editing was removed. The verification diagram was shown in FIG. 2.

Figure 3:
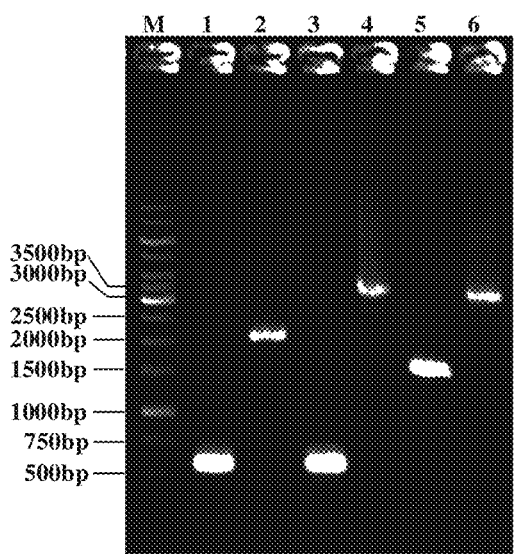
FIG. 3 is an electrophoretogram of yjiT::$P_{trc}$-pta integration where, M denotes a 1 kb Maker; 1 denotes an upstream homologous arm; 2 denotes a target gene; 3 denotes a downstream homologous arm; 4 denotes an overlapped fragment; 5 denotes a PCR fragment of the original strain; and 6 denotes a PCR fragment of the target strain.

2.2 Integration of $P_{trc}$-pta (a Fragment Containing a trc Promoter and pta Gene) on a Pseudogene yjiT Site Using the *E. coli* ATCC27325 genome as a template, upstream homologous arm primers Up-yjiT-S (SEQ ID NO:15), Up-yjiT-A (SEQ ID NO:16) and downstream homologous arm primers DN-yjiT-S (SEQ ID NO:17), DN-yjiT-A (SEQ ID NO:18) were designed according to the upstream and downstream sequences of the gene yjiT, the upstream and downstream homologous arms of the gene yjiT were amplified; primers pta-S (SEQ ID NO:19), pta-A (SEQ ID NO:20) were designed according to the gene pta, and the pta gene fragment was amplified. The promoter $P_{trc}$ was designed in the reverse primer of upstream homologous arm of the gene yjiT and forward primer of the pta gene. The above fragments were subjected to PCR overlapping to obtain an integrated fragment of the gene pta (upstream homologous arm of gene yjiT-$P_{trc}$-pta-downstream homologous arm of gene yjiT); the DNA fragment containing a target sequence for pGRB-yjiT construction was prepared by annealing primers gRNA-yjiT-S (SEQ ID NO:21) and gRNA-yjiT-A (SEQ ID NO:22), then the DNA fragment was recombined with a linearized pGRB vector to obtain a recombinant pGRB-yjiT. The integrated fragment and pGRB-yjiT were electro-transformed into competent cells of an *Escherichia coli* strain constructed in the last step containing a pREDCas9 vector, then the electro-transformed bacterial cells after being resuscitatively cultured were coated on a LB plate containing ampicillin and miramycin, and cultured overnight at 32° C., then a positive recombinant was verified by PCR, and then the pGRB-yjiT for gene editing was removed. The verification diagram was shown in FIG. 3.

Figure 4:
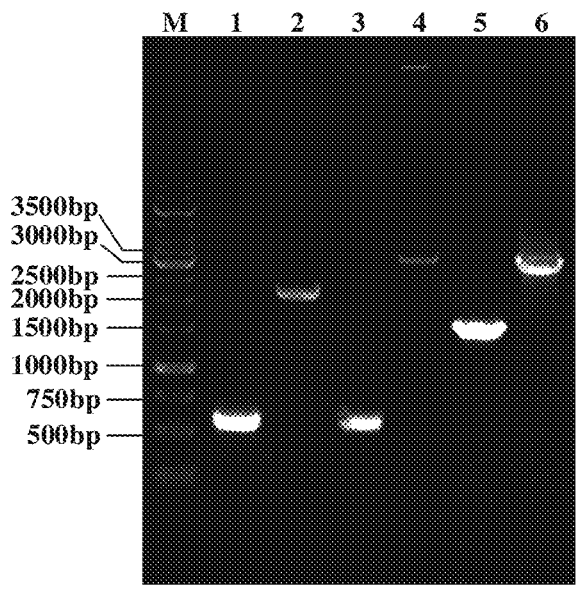
FIG. 4 is an electrophoretogram of yghE::$P_{trc}$-acs integration where, M denotes a 1 kb Maker; 1 denotes an upstream homologous arm; 2 denotes a target gene; 3 denotes a downstream homologous arm; 4 denotes an overlapped fragment; 5 denotes a PCR fragment of the original strain; and 6 denotes a PCR fragment of the target strain.

2.3 Integration of $P_{trc}$-acs (a Fragment Containing a trc Promoter and acs Gene) on a Pseudogene yghE Site Using the *E. coli* ATCC27325 genome as a template, upstream homologous arm primers UP-yghE-S (SEQ ID NO:23), UP-yghE-A (SEQ ID NO:24) and downstream homologous arm primers DN-yghE-S (SEQ ID NO:25), DN-yghE-A (SEQ ID NO:26) were designed according to the upstream and downstream sequences of the gene yghE, the upstream and downstream homologous arms of the gene yghE were amplified; primers acs-S (SEQ ID NO:27) and acs-A (SEQ ID NO:28) were designed according to the gene acs, and the acs gene fragment was amplified. The promoter $P_{trc}$ was designed in the reverse primer of upstream homologous arm of the gene yghE and forward primer of the acs gene. The above fragments were subjected to PCR overlapping to obtain an integrated fragment of the gene acs (upstream homologous arm of gene yghE-$P_{trc}$-acs-downstream homologous arm of gene yghE); the DNA fragment containing a target sequence for pGRB-yghE construction was prepared by annealing primers gRNA-yghE-S (SEQ ID NO:29) and gRNA-yghE-A (SEQ ID NO:30), then the DNA fragment was recombined with a linearized pGRB vector to obtain a recombinant pGRB-yghE. The integrated fragment and pGRB-yghE were electro-transformed into competent cells of an *Escherichia coli* strain constructed in the last step containing a pREDCas9 vector, then the electro-transformed bacterial cells after being resuscitatively cultured were coated on a LB plate containing ampicillin and miramycin, and cultured overnight at 32° C., then a positive recombinant was verified by PCR, and then the pGRB-yghE for gene editing was removed. The verification diagram was shown in FIG. 4.

Figure 5:
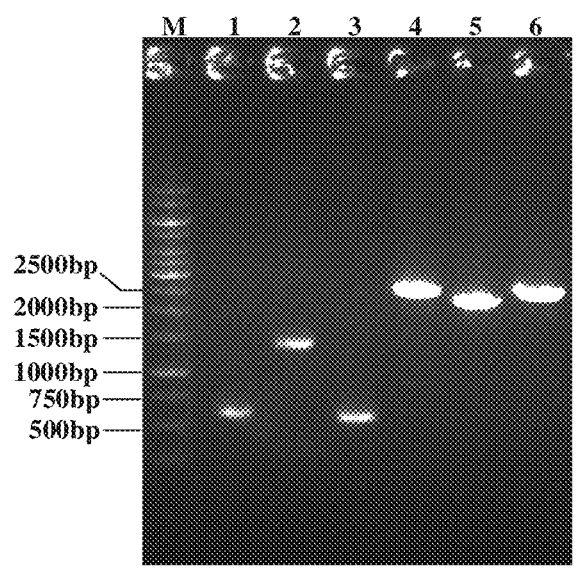
FIG. 5 is an electrophoretogram of ylbE::$P_{trc}$-gltA integration where, M denotes a 1 kb Maker; 1 denotes an upstream homologous arm; 2 denotes a target gene; 3 denotes a downstream homologous arm; 4 denotes an overlapped fragment; 5 denotes a PCR fragment of the original strain; and 6 denotes a PCR fragment of the target strain.

2.4 Integration of $P_{trc}$-gltA (a Fragment Containing a trc Promoter and gltA Gene) on a Pseudogene ylbE Site Using the *E. coli* (ATCC27325) genome as a template, upstream homologous arm primers UP-ylbE-S (SEQ ID NO:31), UP-ylbE-A (SEQ ID NO:32) and downstream homologous arm primers DN-ylbE-S (SEQ ID NO:33), DN-ylbE-A (SEQ ID NO:34) were designed according to the upstream and downstream sequences of the gene ylbE, the upstream and downstream homologous arms of the gene ylbE were amplified; primers gltA-S (SEQ ID NO:35), and gltA-A (SEQ ID NO:36) were designed according to the gene gltA, and the gltA gene fragment was amplified. The promoter $P_{trc}$ was designed in the reverse primer of upstream homologous arm of the gene ylbE and forward primer of the gltA gene. The above fragments were subjected to PCR overlapping to obtain an integrated fragment of the gene gltA (upstream homologous arm of gene ylbE-$P_{trc}$-gltA-downstream homologous arm of gene ylbE); the DNA fragment containing a target sequence for pGRB-yghE construction was prepared by annealing primers gRNA-ylbE-S (SEQ ID NO:37) and gRNA-ylbE-A (SEQ ID NO:38), then the DNA fragment was recombined with a linearized pGRB vector to obtain a recombinant pGRB-ylbE. The integrated fragment and pGRB-ylbE were electro-transformed into competent cells of an *Escherichia coli* strain constructed in the last step containing a pREDCas9 vector, then the electro-transformed bacterial cells after being resuscitatively cultured were coated on a LB plate containing ampicillin and miramycin, and cultured overnight at 32° C., then a positive recombinant was verified by PCR, and then the pGRB-ylbE for gene editing was removed. The verification diagram was shown in FIG. 5.

Figure 6:
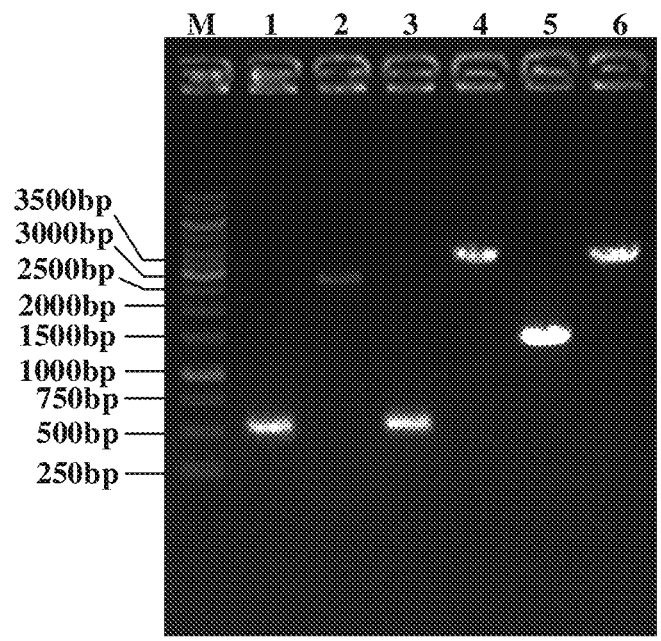
FIG. 6 is an electrophoretogram of yeeL:$P_{trc}$-ppc integration where, M denotes a 1 kb Maker; 1 denotes an upstream homologous arm; 2 denotes a target gene; 3 denotes a downstream homologous arm; 4 denotes an overlapped fragment; 5 denotes a PCR fragment of the original strain; and 6 denotes a PCR fragment of the target strain.

2.5 Integration of $P_{trc}$-ppc (a Fragment Containing a trc Promoter and ppc Gene) on a Pseudogene yeeL Site Using the *E. coli* ATCC27325 genome as a template, upstream homologous arm primers UP-yeeL-S (SEQ ID NO:39), UP-yeeL-A (SEQ ID NO:40) and downstream homologous arm primers DN-yeeL-S (SEQ ID NO:41), DN-yeeL-A (SEQ ID NO:42) were designed according to the upstream and downstream sequences of the gene yeeL; the upstream and downstream homologous arms of the gene yeeL were amplified; primers ppc-S (SEQ ID NO:43), ppc-A (SEQ ID NO:44) were designed according to the gene ppc, and ppc gene fragment was amplified. The promoter $P_{trc}$ was designed in the reverse primer of upstream homologous arm of the gene yeeL and forward primer of the ppc gene. The above fragments were subjected to PCR overlapping to obtain an integrated fragment of the gene ppc (upstream homologous arm of gene yeeL-$P_{trc}$-ppc-downstream homologous arm of gene yeeL); the DNA fragment containing a target sequence for pGRB-yeeL construction was prepared by annealing primers gRNA-yeeL-S (SEQ ID NO:45) and gRNA-yeeL-A (SEQ ID NO:46), then the DNA fragment was recombined with a linearized pGRB vector to obtain a recombinant pGRB-yeeL. The integrated fragment and pGRB-yeeL were electro-transformed into competent cells of an *Escherichia coli* strain constructed in the last step containing a pREDCas9 vector, then the electro-transformed bacterial cells after being resuscitatively cultured were coated on a LB plate containing ampicillin and miramycin, and cultured overnight at 32° C., then a positive recombinant was verified by PCR, and then the pGRB-yeeL for gene editing was removed. The verification diagram was shown in FIG. 6.

2.6 Knockout of the Gene ackA

Figure 7:
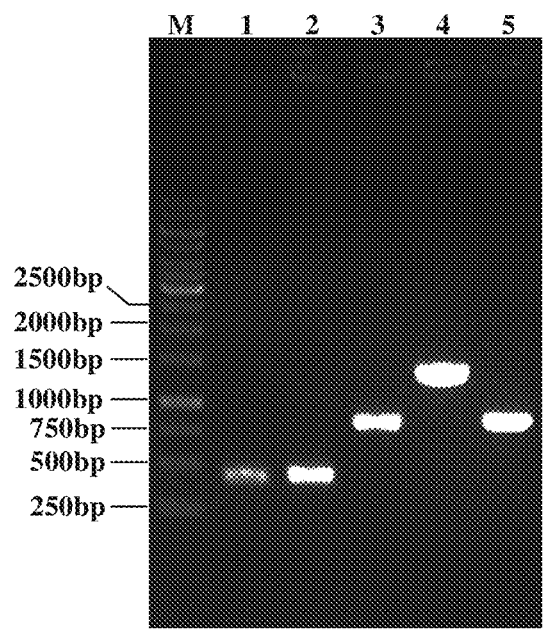
FIG. 7 is an electrophoretogram of ackA knockout where, M denotes a 1 kb Maker; 1 denotes an upstream homologous arm; 2 denotes a downstream homologous arm; 3 denotes an overlapped fragment; 4 denotes a PCR fragment of the original strain; and 5 denotes a PCR fragment of the target strain.

Upstream homologous arm primers UP-ackA-S (SEQ ID NO:47) and UP-ackA-A (SEQ ID NO:48) and downstream homologous arm primers DN-ackA-S (SEQ ID NO:49) and DN-ackA-A (SEQ ID NO:50) were designed according to the upstream and downstream sequences of the gene ackA, and the upstream/downstream homologous arm fragments were amplified by PCR; the above fragments were subjected to PCR overlapping to obtain a gene ackA-knockout fragment (ackA upstream homologous arm-ackA downstream homologous arm). Primers gRNA-ackA-S (SEQ ID NO:51) and gRNA-ackA-A (SEQ ID NO:52) were designed, and the DNA fragment containing the target sequence was amplified, and recombined with a linearized pGRB vector to obtain a recombinant pGRB-ackA. The knockout fragment and pGRB-ackA were electro-transformed into competent cells of an *Escherichia coli* strain constructed in the last step containing a pREDCas9 vector, then the electro-transformed bacterial cells after being resuscitatively cultured were coated on a LB plate containing ampicillin and miramycin, and cultured overnight at 32° C., then a positive recombinant was verified by PCR; and then the pGRB-ackA and pRED-Cas9 for gene editing was removed. The verification diagram was shown in FIG. 7.

And the train *E. coli* THEE was obtained finally.

The order of the above steps may be adjusted according to the actual condition.

3. Primers Used in the Construction Process of the Strain

All the primers involved in the construction process of the strain *E. coli* THEE were shown in the following table:

| SEQ ID NO: | Primer name | Sequence (5'-3') |
|---|---|---|
| 7 | UP-gapC-S | TGGGAAGAAACCACGAAACTC |
| 8 | UP-gapC-A | AATTGTTATCCGCTCACAATTCCACACATTATACGAGCCGGATGATTAATTGTCAATGTTTCAGCAGGTAGGCGAGA |
| 9 | DN-gapC-S | CTGGGCCTTTCGTTTTATCTGTTGTTTGTCGGTGAACGCTCTCCTGAGTAGGACAAATAAAACGGTCGCCTGGTACG |
| 10 | DN-gapC-A | TTATCCGCCGACATTGCTG |
| 11 | xfp-S | TCCGGCTCGTATAATGTGTGGAATTGTGAGCGGATAACAATTTCACACAGGAAACAGACCATGACCTCTCCGGTTATCGGTACCC |
| 12 | xfp-A | ACAAACAACAGATAAAACGAAAGGCCCAGTCTTTCGACTGAGCCTTTCGTTTTATTTGTCATTCGTTGTCACCCGCGGT |
| 13 | gRNA-gapC-S | AGTCCTAGGTATAATACTAGTTATCATTCCCCACACTACGGGTTTTAGAGCTAGAA |
| 14 | gRNA-gapC-A | TTCTAGCTCTAAAACCCCCCGTAGTGTGGGGAATGACTAGTATTATACCTAGGACT |
| 15 | UP-yjiT-S | AATAGTTGTTGCCGCCTGAGTAACT |
| 16 | UP-yjiT-A | AATTGTTATCCGCTCACAATTCCACACATTATACGAGCCGGATGATTAATTGTCAAGCAGCCAGTAATCTTCCATCCCTTT |
| 17 | DN-yjiT-S | AAAGACTGGGCCTTTCGTTTTATCTGTTGTTTGTCGGTGAACGCTCTCCTGAGTAGGACAAATATCGGATTCGCACCGGAAGAGA |
| 18 | DN-yjiT-A | TGTCCCGTGCCAGAAGATGAGG |
| 19 | pta-S | TCCGGCTCGTATAATGTGTGGAATTGTGAGCGGATAACAATTTCACACAGGAAACAGACCGTGTCCCGTATTATTATGCTG |
| 20 | pta-A | CACCGACAAACAACAGATAAAACGAAAGGCCCAGTCTTTCGACTGAGCCTTTCGTTTTATTTGTTACTGCTGCTGTGCAGACTG |
| 21 | gRNA-yjiT-S | AGTCCTAGGTATAATACTAGTAGGGATTATGAACGGCAATGGTTTTAGAGCTAGAA |
| 22 | gRNA-yjiT-A | TTCTAGCTCTAAAACCATTGCCGTTCATAATCCCTACTAGTATTATACCTAGGACT |
| 23 | UP-yghE-S | GGCGATTGCTACTGCTGATGCT |
| 24 | UP-yghE-A | AATTGTTATCCGCTCACAATTCCACACATTATACGAGCCGGATGATTAATTGTCAACCCAATACTGGGCGAAGGGAGA |
| 25 | DN-yghE-S | AAAGACTGGGCCTTTCGTTTTATCTGTTGTTTGTCGGTGAACGCTCTCCTGAGTAGGACAAATCGCTGCCAAGGACTCTGAGGAT |
| 26 | DN-yghE-A | TAGGGCATTGGGAGGGCGATTT |
| 27 | acs-S | TCCGGCTCGTATAATGTGTGGAATTGTGAGCGGATAACAATTTCACACAGGAAACAGACCATGAGCCAAATTCACAAACAC |
| 28 | acs-A | CACCGACAAACAACAGATAAAACGAAAGGCCCAGTCTTTCGACTGAGCCTTTCGTTTTATTTGTTACGATGGCATCGCGATAGC |
| 29 | gRNA-yghE-S | AGTCCTAGGTATAATACTAGTCATTACCACTTATGGCGAACGTTTTAGAGCTAGAA |
| 30 | gRNA-yghE-A | TTCTAGCTCTAAAACGTTCGCCATAAGTGGTAATGACTAGTATTATACCTAGGACT |
| 31 | UP-ylbE-S | ACCCAACCTTACGCAACCAG |
| 32 | UP-ylbE-A | AATTGTTATCCGCTCACAATTCCACACATTATACGAGCCGGATGATTAATTGTCAATTGTTCGATAACCGCAGCAT |
| 33 | DN-ylbE-S | AAAGACTGGGCCTTTCGTTTTATCTGTTGTTTGTCGGTGAACGCTCTCCTGAGTAGGACAAATCGCTGGCGTGCTTTGAA |

-continued

| SEQ ID NO: | Primer name | Sequence (5'-3') |
|---|---|---|
| 34 | DN-ylbE-A | GGCGTAACTCAGCAGGCAG |
| 35 | gltA-S | TCCGGCTCGTATAATGTGTGGAATTGTGAGCGGATAACAATTTCACACAGG AAACAGACCATGGCTGATACAAAAGCAAAACTC |
| 36 | gltA-A | CACCGACAAACAACAGATAAAACGAAAGGCCCAGTCTTTCGACTGAGCC TTTCGTTTTATTTGTTAACGCTTGATATCGCTTTTAAAG |
| 37 | gRNA-ylbE-S | AGTCCTAGGTATAATACTAGTACACTGGCTGGATGTGCAACGTTTTAGAGC TAGAA |
| 38 | gRNA-ylbE-A | TTCTAGCTCTAAAACGTTGCACATCCAGCCAGTGTACTAGTATTATACCTAG GACT |
| 39 | UP-yeeL-S | TTCATCGGGACGAGTGGAGA |
| 40 | UP-yeeL-A | AATTGTTATCCGCTCACAATTCCACACATTATACGAGCCGGATGATTAATTG TCAACCATAGCATCGCCAATCTGA |
| 41 | DN-yeeL-S | CTGGGCCTTTCGTTTTATCTGTTGTTTGTCGGTGAACGCTCTCCTGAGTAG GACAAATACCCAAAGGTGAAGATAAAGCC |
| 42 | DN-yeeL-A | CATTCCCTCTACAGAACTAGCCCT |
| 43 | ppc-S | TCCGGCTCGTATAATGTGTGGAATTGTGAGCGGATAACAATTTCACACAGG AAACAGACCATGAACGAACAATATTCCGCAT |
| 44 | ppc-A | ACAAACAACAGATAAAACGAAAGGCCCAGTCTTTCGACTGAGCCTTTCGT TTTATTTGTTAGCCGGTATTACGCATACCT |
| 45 | gRNA-yeeL-S | AGTCCTAGGTATAATACTAGTAACACAGCAATACGGTACGCGTTTTAGAGC TAGAA |
| 46 | gRNA-yeeL-A | TTCTAGCTCTAAAACGCGTACCGTATTGCTGTGTTACTAGTATTATACCTAG GACT |
| 47 | UP-ackA-S | ACTGGTTCTGAACTGCGGTAGT |
| 48 | UP-ackA-A | TGTAAGGCAGGGCGTAGAGGTA |
| 49 | DN-ackA-S | AATGCCGCAATGGTTCGTGAA |
| 50 | DN-ackA-A | GCCGTCGTGGTGGAAGAGTT |
| 51 | gRNA-ackA-S | AGTCCTAGGTATAATACTAGTCTTCTATGTAACCCAGGAAGGTTTTAGAGCT AGAA |
| 52 | gRNA-ackA-A | TTCTAGCTCTAAAACCTTCCTGGGTTACATAGAAGACTAGTATTATACCTAG GACT |

Example 2: Fermentation of L-Theanine Via the Strain *E. coli* THEE in a 5 L Fermentation Tank The slant medium consists of: 2 g/L glucose, 6 g/L peptone, 6 g/L beef extract, 3 g/L yeast powder, 2 g/L sodium chloride, and 18 g/L agar with a pH of 7.0.

The seed medium consists of: 25 g/L glucose, 6 g/L yeast extract, 15 g/L peptone, 15 g/L sodium chloride and the rest is water, wherein a pH value is 7.0.

The fermentation medium consists of: 30 g/L glucose, 6 g/L yeast powder, 8 ml/L corn syrup, 1.5 g/L citric acid, 2.5 g/L monopotassium phosphate, 2.0 g/L dipotassium phosphate, 1.0 g/L magnesium sulfate, and the rest is water, wherein a pH value is 7.2.

(1) Slant culture: a loop of bacterium was scratched from a bacterial tube in a −80° C. refrigerator, evenly coated on an activated slant, cultured for 14 h at 37° C., and transferred to an eggplant-shaped flask for continuous culture for 14 h;

(2) seed culture: a proper amount of sterile water was taken to an eggplant-shaped flask, and a bacterial suspension was inoculated into the seed medium, a pH value was stabilized 7.0 around, and a temperature of 37° C. and dissolved oxygen were kept within 30-34%, and cells were cultured to a dry cell weight of 6 g/L;

(3) fermentation cultivation: a seed solution was inoculated into a fresh fermentation medium by 12% inoculum size, wherein a pH value was controlled at 7.0 during the fermentation, a temperature was maintained at 36° C., and a dissolved oxygen was within 25-30%; 600 g/L glucose solution was added by a fed-batch way to maintain a glucose concentration in the fermentation medium less than 1 g/L after glucose in the medium was completely consumed.

To compare the influences of the different feeding ways of ethylamine on the fermentation results, a control group and an experimental group were set as follows:

a fed-batch way of ethylamine commonly used in the art was taken in the control group, namely, when $OD_{600}$=20, 2 mol/L ethylamine solution was added with a constant speed of 30 mL/h to the end of the fermentation;

an OD-linked ethylamine supplementary strategy was taken in the experimental group; the fed-batch rate of ethylamine $(g·L^{-1}·h^{-1})$=0.5×$OD_{600\ nm}$/(volume of the fermentation broth (L)×fermentation time (h)); when $OD_{600\ nm}$ was above 10, addition of ethylamine was started, and the fed-batch rate of ethylamine was adjusted per hour for once.

Figure 8:
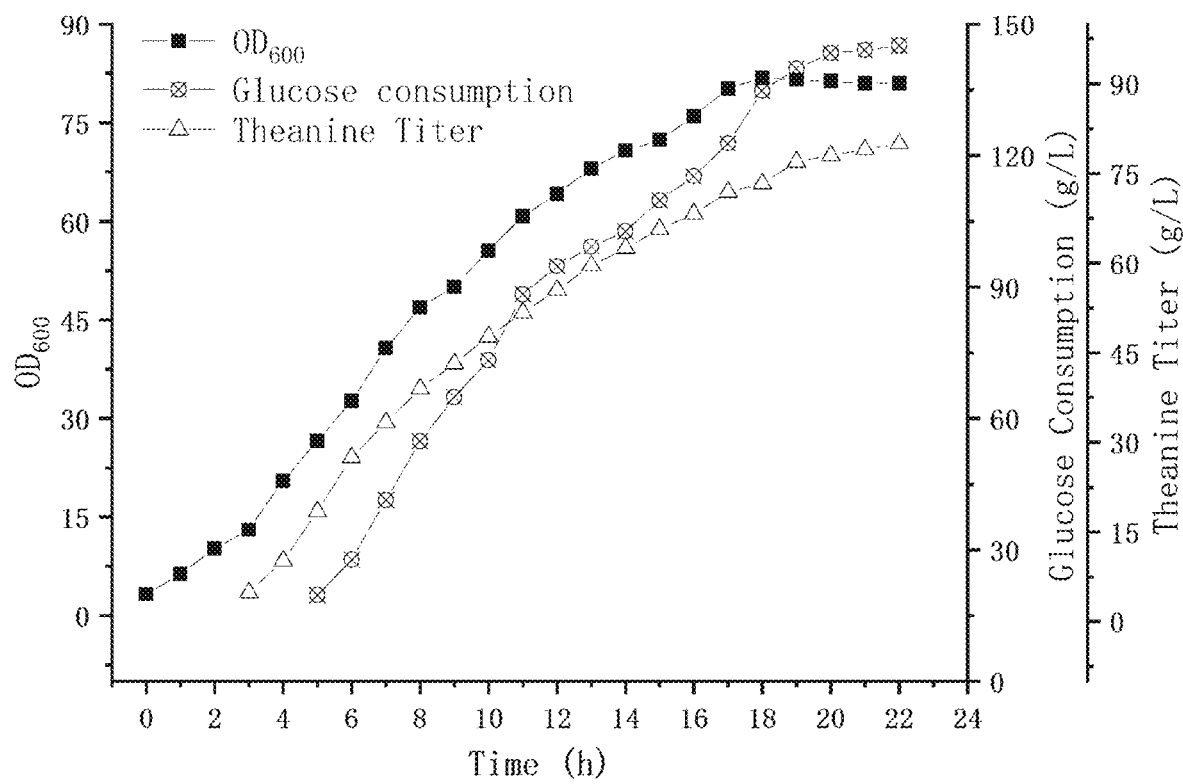
FIG. 8 is a fermentation process curve of the genetically engineered bacterium *Escherichia coli* THEE in 5 L fermentation tank.

After 22 h of fermentation in a 5 L fermentation tank, the titer and the yield of L-theanine were shown in the table below; the fermentation process curve of the experimental group was shown in FIG. 8 (the yield of the present invention was as follows: (titer of L-theanine/consumption of glucose)×100%):

| Groups | Titer of L-theanine (g/L) | Yield (%) | Maximum $OD_{600\,nm}$ value |
|---|---|---|---|
| Experimental group | 80 ± 2.5 | 55 ± 1.2 | 81 ± 2.6 |
| Control group | 72 ± 2.1 | 50 ± 1.3 | 53 ± 3.5 |

Example 3 Determination of the OD-Linked Ethylamine Supplementary Strategy

L-theanine was produced by fermentation in a 5 L fermentation tank; when $OD_{600\,nm}$ was above 10, addition of ethylamine was started; the ethylamine fed-batch speed was adjusted at different degrees per hour according to the consumption degree of glucose, thus ensuring that the sugar consumption rate was kept within 7-8 $g \cdot L^{-1} \cdot h^{-1}$. Reports of 50 fermentation batches whose L-theanine titer was up to 80 g/L were collected to calculate the average $OD_{600\,nm}$ value, average volume of the fermentation broth and the average ethylamine fed-batch rate at different fermentation time, as shown in the table below:

| Fermentation time (h) | Average $OD_{600\,nm}$ value | Average of the fermentation broth (L) | Average ethylamine fed-batch rate $(g \cdot L^{-1} \cdot h^{-1})$ |
|---|---|---|---|
| 1 | 6.38 | 2 | 0 |
| 2 | 10.2 | 2 | 1.29 |
| 3 | 15.05 | 2 | 1.25 |
| 4 | 20.55 | 2.1 | 1.22 |
| 5 | 26.6 | 2.2 | 1.2 |
| 6 | 32.6 | 2.3 | 1.18 |
| 7 | 40.7 | 2.5 | 1.16 |
| 8 | 46.9 | 2.6 | 1.12 |
| 9 | 50 | 2.7 | 1.03 |
| 10 | 55.6 | 2.8 | 0.99 |
| 11 | 60.8 | 2.9 | 0.95 |
| 12 | 64.2 | 2.9 | 0.92 |
| 13 | 68 | 3 | 0.87 |
| 14 | 70.8 | 3 | 0.84 |
| 15 | 72.4 | 3 | 0.8 |
| 16 | 76 | 3.1 | 0.76 |
| 17 | 80.2 | 3.1 | 0.75 |
| 18 | 81.8 | 3.1 | 0.73 |
| 19 | 81.5 | 3.2 | 0.67 |
| 20 | 81.3 | 3.2 | 0.63 |
| 22 | 81 | 3.2 | 0.57 |

Figure 9:
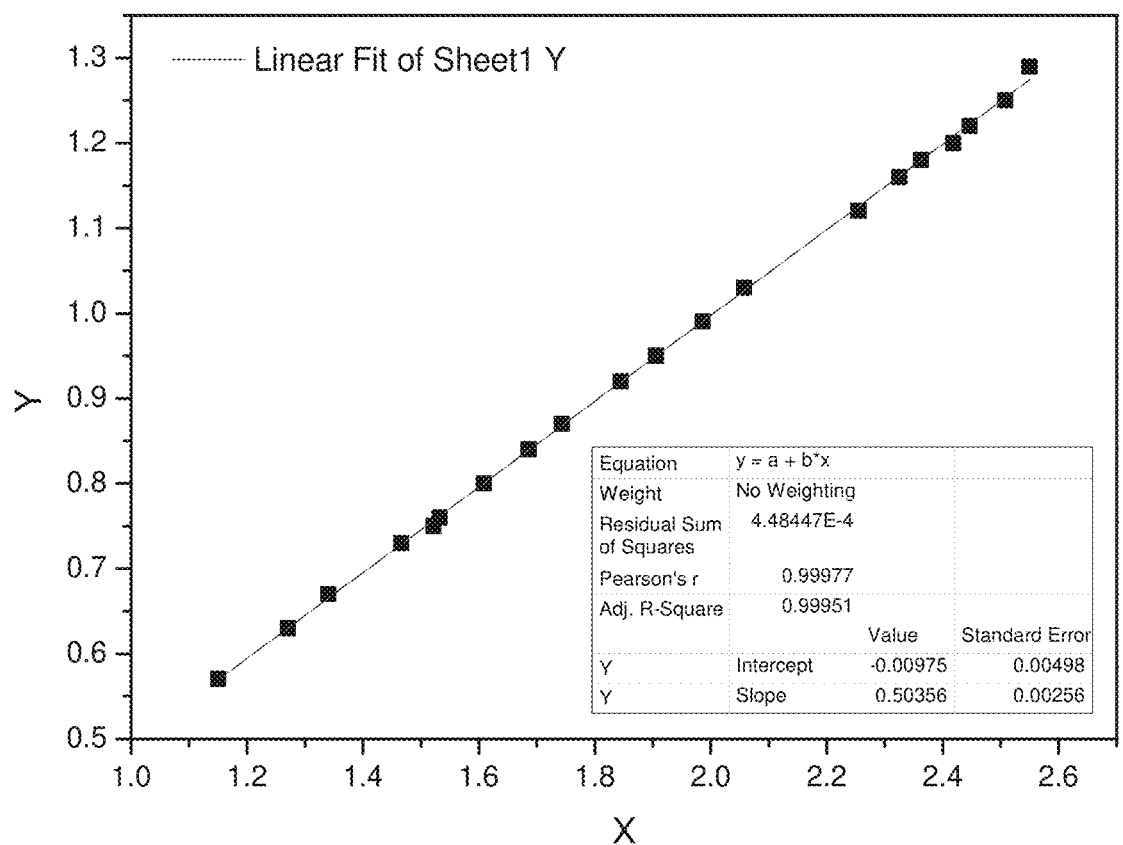
FIG. 9 is a linear fitting diagram of ethylamine flow rate.

ORIGIN software was used for linear fitting according to the data in the above table. Y denotes average ethylamine fed-batch rate, X denotes average $OD_{600\,nm}$ value/(average volume of the fermentation broth (L)×fermentation time (h). The fitting result was shown in FIG. 9. An OD-linked ethylamine supplementary strategy was taken according to the fitted equation; namely, the fed-batch rate of ethylamine $(g \cdot L^{-1} \cdot h^{-1})$=0.5×$OD_{600\,nm}$ value/(volume of the fermentation broth (L)×fermentation time (h)).

Example 4 Separation and Extraction of L-Theanine from the Fermentation Broth (1) The fermentation broth with a total volume of 3.2 L was obtained at the end of the fermentation in Example 2, and the L-theanine content was 80 g/L, 256 g in total. The fermentation broth was heated up to 60° C. and maintained for 30 min, then cooled to 35° C. The L-theanine fermentation broth was subjected to microfiltration with a 50 nm ceramic membrane for sterilization and a filtrate was collected, and water in 0.8 times the volume of the fermentation broth was supplemented when the filtrate had a flow rate lower than 5 mL/min at pressure of 0.2 MPa, and when the L-theanine had a concentration less than 1.3 g/L in retentate solution, the microfiltration of ceramic membrane was over.

(2) 5.1 L ceramic membrane filtrate (L-theanine content was 48.8 g/L) was sieved with a 001×7 cationic resin to adsorb L-theanine with an adsorbing capacity of 160 g (L-theanine)/L (resin), then 0.6% ammonia water was used for elution and collection, the obtained eluent had a volume of 4.6 L (L-theanine content was 52.9 g/L). The eluent was sieved with a D213 anion resin to adsorb pigments and 4.8 L resin effluent (L-theanine content was 49.3 g/L) was collected.

(3) The resin effluent was pumped into a decoloring tank, and a pharmaceutical activated carbon (4.7 g) with 2% mass of the L-theanine was added for decolorization until a feed liquid had a light transmittance of 98%. The decoloring solution was pumped into an evaporator for concentration under reduced pressure until a volume of 600 mL (L-theanine content was 364.2 g/L), where a vacuum degree of −0.08 MPa and a temperature of 60° C. were maintained.

(4) A concentrated solution was pumped into a crystallizer, and 240 mL 95% ethanol was added and cooled in vacuum and crystallized, centrifuged and separated to obtain 820 mL crystallization mother liquor; 215.0 g wet crystals were collected with a water content of 13.9%, and dried to obtain 185 g L-theanine final product with a one-step crystallization yield of 72.3%. Detected by liquid chromatography, the final product had a purity of 99%.

Example 5: Fermentation of L-Theanine Via the Strain *E. coli* THEE in a 5 L Fermentation Tank The slant medium consists of: 1 g/L glucose, 5 g/L peptone, 5 g/L beef extract, 1 g/L yeast powder, 1 g/L sodium chloride, and 15 g/L agar with a pH of 7.0-7.2;

the seed medium consists of: 20 g/L glucose, 5 g/L yeast extract, 10 g/L peptone, 10 g/L sodium chloride and the rest is water, wherein a pH value is 7.0-7.2;

the fermentation medium consists of: 10 g/L glucose, 2 g/L yeast powder, 2 ml/L corn syrup, 0.2 g/L citric acid, 0.5 g/L monopotassium phosphate, 0.5 g/L dipotassium phosphate, 0.2 g/L magnesium sulfate, and the rest is water, wherein a pH value is 7.0-7.2.

(1) Slant culture: a loop of bacterium was scratched from a bacterial tube in a −80° C. refrigerator, evenly coated on an activated slant, cultured for 16 h at 37° C., and transferred to an eggplant-shaped flask for continuous culture for 16 h;

(2) seed culture: a proper amount of sterile water was taken to the eggplant-shaped flask, and a bacterial suspension was inoculated into a seed medium, a pH value was stabilized 7.0 around, and a temperature of 37° C. and dissolved oxygen were kept within 25-35%, and cells were cultured to a dry cell weight of 5 g/L;

(3) fermentation cultivation: a seed solution was inoculated into a fresh fermentation medium by 15% inoculum size, where a pH value was controlled within 6.7-7.2 during the fermentation, a temperature was maintained at 28° C., and a dissolved oxygen was within 10-30%; 600 g/L glucose solution was added by a fed-batch way to maintain a glucose concentration in the fermentation medium less than 1 g/L after glucose in the medium was completely consumed;

an OD-linked ethylamine supplementary strategy was taken; the fed-batch rate of ethylamine $(g \cdot L^{-1} \cdot h^{-1})=0.5 \times OD_{600\ nm}$/(volume of the fermentation broth (L)×fermentation time (h)); when $OD_{600\ nm}$ was above 10, addition of ethylamine was started, and the fed-batch rate of ethylamine was adjusted per hour for once.

After 20 h of fermentation in a 5 L fermentation tank, L-theanine had a titer of 75 g/L and a yield of 52%.

Example 6: Fermentative Production of L-Theanine Via the Strain E. coli THEE in a 5 L Fermentation Tank The slant medium consists of: 5 g/L glucose, 10 g/L peptone, 10 g/L beef extract, 5 g/L yeast powder, 2.5 g/L sodium chloride, and 20 g/L agar with a pH of 7.0-7.2;

the seed medium consists of: 30 g/L glucose, 10 g/L yeast extract, 20 g/L peptone, 20 g/L sodium chloride and the rest is water, wherein a pH value is 7.0-7.2;

the fermentation medium consists of: 40 g/L glucose, 8 g/L yeast powder, 20 ml/L corn syrup, 2.0 g/L citric acid, 3.2 g/L monopotassium phosphate, 2.4 g/L dipotassium phosphate, 1.2 g/L magnesium sulfate, and the rest is water, wherein a pH value is 7.0-7.2;

(1) slant culture: a loop of bacterium was scratched from a bacterial tube in a −80° C. refrigerator, evenly coated on an activated slant, cultured for 12 h at 37° C., and transferred to an eggplant-shaped flask for continuous culture for 12 h;

(2) seed culture: a proper amount of sterile water was taken to an eggplant-shaped flask, and a bacterial suspension was inoculated into the seed medium, a pH value was stabilized 7.0 around, and a temperature of 37° C. and dissolved oxygen were kept within 25-35%, and cells were cultured to a dry cell weight of 6 g/L;

(3) fermentation cultivation: a seed solution was inoculated into a fresh fermentation medium by 12% inoculum size, where a pH value was controlled within 6.7-7.2 during the fermentation, a temperature was maintained at 35° C., and a dissolved oxygen was within 10-30%; 600 g/L glucose solution was added by a fed-batch way to maintain a glucose concentration in the fermentation medium less than 1 g/L after glucose in the medium was completely consumed;

an OD-linked ethylamine supplementary strategy was taken; the fed-batch rate of ethylamine $(g \cdot L^{-1} \cdot h^{-1})=0.5 \times OD_{600\ nm}$/(volume of the fermentation broth (L)×fermentation time (h)); when $OD_{600\ nm}$ was above 10, addition of ethylamine was started, and the fed-batch rate of ethylamine was adjusted per hour for once.

After 25 h of fermentation in a 5 L fermentation tank, L-theanine had a titer of 77 g/L and a yield of 53%.

The above examples are merely used to express several embodiments of the present invention and described more specifically, but are not construed as limiting the scope of the patent. It should be indicated that a person skilled in the art may make several transformations, combinations and improvements of the above examples within the idea of the patent, and these transformations, combinations and improvements shall fall within the protection scope of the patent. Therefore, the protection scope of the patent shall be subjected to the claims.

What is claimed is:

1. A genetically engineered bacterium producing L-theanine, wherein the genetically engineered bacterium is obtained by using a strain as an original strain, wherein the original strain is obtained after integrating a single copy of a RNA polymerase gene T7RNAP, a dual copy of a γ-glutamylmethylamide synthetase gene gmas, and a knockout of a xylose operon transcription factor gene xylR and a knockout of a succinyl-CoA synthetase gene sucCD on a genome of *Escherichia coli* W3110, and then by integrating an exogenous fructose 6-phosphate phosphoketolase gene xfp, an exogenous phosphoacetyl transferase gene pta, an exogenous acetyl-CoA synthetase gene acs, an exogenous citrate synthase gene gltA, and an exogenous phosphoenolpyruvate carboxylase gene ppc on the genome, and knocking out an acetokinase gene ackA.

2. The genetically engineered bacterium of claim 1, wherein the fructose 6-phosphate phosphoketolase gene xfp comprising the nucleotide sequence as shown in SEQ ID NO: 1; the phosphoacetyl transferase gene pta comprising the nucleotide sequence as shown in SEQ ID NO:2; the acetyl-CoA synthetase gene acs comprising the nucleotide sequence as shown in SEQ ID NO:3; the citrate synthase gene gltA comprising the nucleotide sequence as shown in SEQ ID NO:4; the phosphoenolpyruvate carboxylase gene ppc comprising the nucleotide sequence as shown in SEQ ID NO:5; and the acetokinase gene ackA comprising the nucleotide sequence as shown in SEQ ID NO:6.

3. The genetically engineered bacterium of claim 1, wherein genes xfp, pta, acs, gltA, and ppc are respectively controlled by a trc promoter.

* * * * *